(12) United States Patent  (10) Patent No.: US 7,449,315 B2
Gilbert et al.  (45) Date of Patent: *Nov. 11, 2008

(54) BIFUNCTIONAL ENERGY-REVERSIBLE ACYL-COMPOSITIONS

(75) Inventors: Carl W. Gilbert, Powder Springs, GA (US); Eleanor B. McGowan, Smyrna, GA (US); Kirby S. Black, Acworth, GA (US); T. Gregory P. Harper, Stockton, CA (US)

(73) Assignee: Cryolife, Inc., Kennesaw, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/694,023

(22) Filed: Mar. 30, 2007

(65) Prior Publication Data

US 2007/0167644 A1  Jul. 19, 2007

Related U.S. Application Data

(62) Division of application No. 11/324,053, filed on Dec. 30, 2005, which is a division of application No. 10/066,323, filed on Jan. 31, 2002, now Pat. No. 7,157,458.

(51) Int. Cl.
*C12N 9/00* (2006.01)
*A61K 47/00* (2006.01)
*A61K 31/704* (2006.01)
*A61K 31/495* (2006.01)
*C07C 57/44* (2006.01)

(52) U.S. Cl. .................. 435/183; 514/34; 514/396; 514/529; 514/252.12; 514/773; 514/785; 514/568; 514/554; 514/613; 514/614; 564/164; 564/167; 560/45; 548/542; 544/358

(58) Field of Classification Search ............... None
See application file for complete search history.

(56) References Cited

U.S. PATENT DOCUMENTS

| | | |
|---|---|---|
| 4,235,887 A | 11/1980 | Voorhees et al. |
| 4,302,457 A | 11/1981 | Voorhees et al. |
| 4,625,014 A | 11/1986 | Senter et al. |
| 5,114,851 A | 5/1992 | Porter et al. |
| 5,218,137 A | 6/1993 | Porter et al. |
| 5,266,453 A | 11/1993 | Matushita et al. |
| 5,585,499 A | 12/1996 | Chari et al. |
| 5,624,711 A | 4/1997 | Sundberg et al. |
| 5,763,504 A | 6/1998 | Matsuda et al. |
| 5,846,545 A | 12/1998 | Chari et al. |
| 5,917,016 A | 6/1999 | Holmes |
| 5,986,076 A | 11/1999 | Rothschild et al. |
| 6,025,444 A | 2/2000 | Waki et al. |

(Continued)

OTHER PUBLICATIONS

Ng. H.P., et al., Design, synthesis, and biological activity of novel factor Xa inhibitors: 4-aryloxy substituents of 2, 6-diphenoxypyridines, Bioorg Med Chem 2002, 10(3): 657-66.

(Continued)

*Primary Examiner*—Brian J Davis
(74) *Attorney, Agent, or Firm*—Lucas & Mercanti, LLP

(57) ABSTRACT

Energy-reversible acyl conjugates, intermediates, and related compositions are disclosed. In preferred aspects, examples of such compositions include:

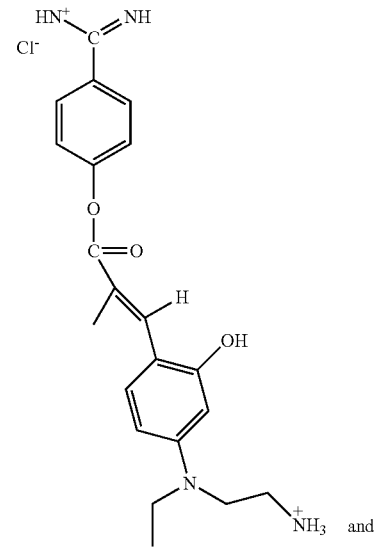

and

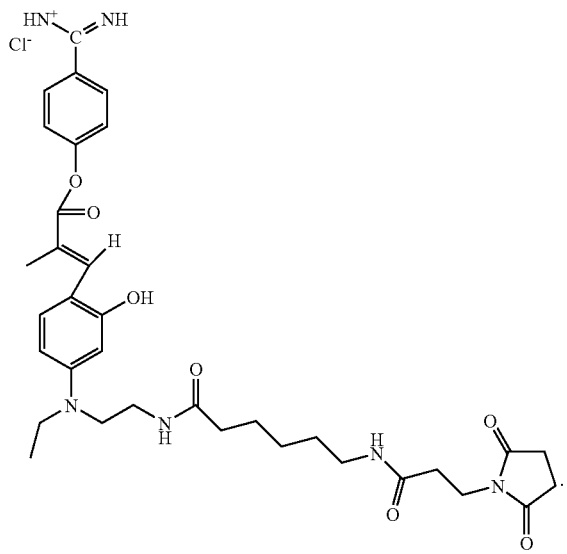

31 Claims, 6 Drawing Sheets

U.S. PATENT DOCUMENTS

| | | | |
|---|---|---|---|
| 6,057,096 | A | 5/2000 | Rothschild et al. |
| 6,107,410 | A | 8/2000 | Waki et al. |
| 6,774,116 | B2 * | 8/2004 | Gilbert et al. ............... 514/34 |
| 7,157,458 | B2 * | 1/2007 | Gilbert et al. ............... 514/247 |
| 2006/0106204 | A1 * | 5/2006 | Gilbert et al. ............ 530/391.1 |

OTHER PUBLICATIONS

Antczak, C., et al., A new acivicin prodrug designed for tumor-targeted delivery, Bioorg Med Chem 2001, 9(11): 2843-8.

Thuring, J.W., et al., Comparative study of the active site caging of serine proteases: thrombin and factor Xa, Biochemistry Feb. 12, 2002, 41(6): 2002-13.

Porter, N.A., et al., Photo-reversible binding of thrombin to avidin by means of a photolabile inhibitor, J Photochem Photobiol B 1997, 38(1): 61-9.

Matsuda, T., et al., Newly designed tissue adhesion prevention technology based on photocurable mucopolysaccharides. In vivo evaluation., ASAIO J 1993, 3 (3): M327-31.

Porter, N.A., et al., Photochemistry of enzyme-bound cinnamoyl derivatives, Apr. 1993, J. Am. Chem. Soc. 115: 9371-9379.

6 Office Actions issued from USPTO, U.S. Appl. No. 10/066,323, now issued as Patent No. 7,157,458.

1 Office Action issued from USPTO, U.S. Appl. No. 11/324,053.

International Search Report and Interantional Preliminary Examination Report for PCT International Application No. PCT/US02/11476.

* cited by examiner

BIFUNCTIONAL ENERGY-REVERSIBLE ACYL-COMPOSITIONS

CROSS-REFERENCE TO RELATED APPLICATIONS

This is a divisional of U.S. patent application Ser. No. 11/324,053 filed Dec. 30, 2005, which is a divisional of U.S. patent application Ser. No. 10/066,323 filed Jan. 31, 2002, now U.S. Pat. No. 7,157,458 which, in turn, claims the benefit of priority from U.S. Provisional Patent Application No. 60/284,308, filed Apr. 17, 2001, the contents of each of which are incorporated herein by reference in its entirety.

BACKGROUND OF THE INVENTION

The present application relates generally to energy reversible acyl-enzymes. In particular, the present application relates to energy reversible acyl-enzymes and the like having a cinnamate or related structure core and an additional reactive group which can be modified to impart new properties to the whole composition.

Various methods to make use of enzyme inactivation have been disclosed. Enzyme inhibition can be used to enhance long term storage of enzymes or to inactivate the enzymes in a pharmaceutical drug. For example, U.S. Pat. No. 5,770,699 describes a process of enzyme inhibition to produce inactivated blood factors. U.S. Pat. No. 5,837,679 discloses a method to extend the half lives of blood factors via a transient modification of blood factors by acylation. U.S. Pat. No. 4,337,244 reports a method of treating venous thrombosis using an inactivated fibrinolytic enzyme.

Enzyme activity can be controlled with inhibitors. Reversible control of enzyme activity with light has been the focus of a number of reports (see U.S. Pat. Nos. 5,114,851 and 5,218,137 to Porter et al.). There are a number of advantages of this concept. Most stricing is the ability to control enzyme activity specifically and rapidly, by exposure to light in vivo or ex vivo.

Porter et al. disclose in U.S. Pat. Nos. 5,114,851 and 5,218,137, the light controllable enzymes are obtained by coupling an enzyme active site amino acid residue to cinnamate (CINN) derivatives to form o-hydroxy cinnamate substituted esters or acyl enzymes, which are inactive. On photolysis, the bond with the active site amino acid residue is cleaved and the active site is exposed. Pizzo et al. [(1986) Ann. N.Y. Acad. Sci. 485: 199-203] reported on the use of an o-hydroxy cinnamate substituted ester, formed by coupling the active site of an enzyme to α-methyl-2-hydroxy-4-diethylaminocinnamic acid.

A subsequent report by Porter, et al. demonstrated the therapeutic potential of the inhibited enzymes. Control of clotting reaction times was concentration dependent and photolysis time dependent. In vivo clotting of abnormal blood vessels in a rabbit model of corneal neovascularization was achieved by injection of the inhibited, "caged" enzymes and application of 366 nm light to the eyes for 25 minutes. See Arroyo et al., Thromb. Haemost. 78, 791-793 (1997). U.S. Pat. Nos. 5,114,851 and 5,218,137, further describe these cinnamate derivatized enzymes and uses thereof.

The usefulness of the inhibited enzymes is a function of the rate and extent of photolysis. Utility is limited if rate of bond cleavage between the cirtamate moiety and the active-site amino acid is slow. Many applications require rapid exposure times, on the order of seconds in most in vitro or typical applications, or at most minutes, in most in vivo applications. Rapid, controlled response times are essential for most clinical applications and are of particular importance with labile enzymes or uses where rapid reaction times are essential, as in clotting.

For example, the formation of an acyl-enzyme between α-chymotrypsin and the p-nitrophenyl ester of p-nitro-trans-cinnamic acid is described by Varfolomeyev, S., et al., [FEBS Lett. 15:118 (1971)]. The bond between the enzyme and the carboxylate group is formed with the hydroxyl group of the serine at the catalytic center of the enzyme [Berezin, I. et al., FEBS Lett. 8:173 (1970)]. The formation of an acyl-enzyme between a-thrombin and the trans-isomer of an ester of o-hydroxy-a-methylcinnamic acid is described by Turner, A., et al., J. Amer. Chem. Soc.109:1274 (1987). The bond between the enzyme and the carboxylate group is formed with the hydroxyl group of the serine-195 at the catalytic center of the enzyme (Turner, A., et al., J. Amer. Chem. Soc. 110:244 (1988)). Exposure of the compound to light led to deacylation. The photoactivation of these enzymes was slow and required light intensities and wavelengths such that appreciable enzyme degradation occurred during photoactivation.

Research in this area has continued. For example, Porter, et al. (Photochem. Photobiol. B 38(1), 61-69 (1997) inserted a biotin derivative on the 2-position of the cinnamate side chain (adjacent to the carboxylate group), which could be bound to avidin, for purposes of purification and immobilization. The modified compound also maintained the ability to be photo-activatable.

Further modifications of the CINN core molecule would be desirable in order to improve inhibited enzyme compositions that can be rapidly and controllably reactivated. For example, it would be desirable to introduce additional sites to react with other molecules for purposes of changing the properties of the acyl-enzyme (such as immobilization or pharmacokinetics), while maintaining the desired properties of photo-activation. The present invention addresses this need.

SUMMARY OF THE INVENTION

It is an object of the present invention to provide improved compositions designated herein as Z-CINN-$X_1$-A, including inhibited enzymes that can be rapidly and controllably reactivated.

It is another object of the present invention to provide an additional site on Z-CINN-$X_1$-A type compounds (as defined below) which can be derivatized in various ways, including with groups designated herein as "B-L", to provide compositions designated herein as B-L-Z-CINN-$X_1$-A, with additional properties such as stability, targeting capacity, or immobilization to appropriate supports.

It is yet another object of the present invention to provide an enzyme inhibitor composition (B-L-Z-CINN-$X_1$-$A_1$), which is capable of generating an inactivated enzyme composition (B-L-Z-CINN-$X_1$-$A_2$), where the enzyme can be released in active form via a controlled mechanism such as input of light energy.

These and other objects are provided by the present invention which in one embodiment provides compositions corresponding to Z-CINN-$X_1$-A and Formula (I):

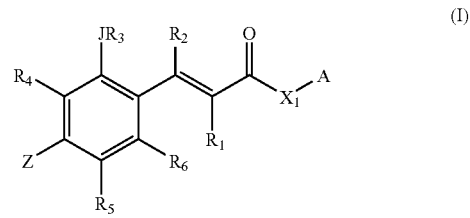

wherein:

$R_1$ and $R_2$ are individually selected from among H, $CH_3$, $C_2$-$C_{10}$alkyls, alkenyls or alkynyls which can be substituted or unsubstituted; straight or branched; $C_2$-$C_{10}$ heteroalkyls, heteroalkenyls or heteroajkynyls and —$(CR_{15}R_{16})_p$-D,
  wherein: $R_{15}$ and $R_{16}$ are individually selected from the group consisting of H, $CH_3$, $C_2$-$C_{10}$ alkyls, alkenyls or alkynyls which can be substituted or unsubstituted; straight or branched; $C_2$-$C_{10}$ heteroalkyls, heteroalkenyls or heteroalkynyls;
  p is a positive integer from 1 to about 12;
  D is selected from among —SH, —OH, $X_2$, —CN, —$OR_{19}$, $NHR_{20}$, wherein:
  $R_{17}$ is H, $CH_3$ or $X_3$;
  $R_{18}$ is H, a $C_1$-$C_4$ alkyl or benzyl;
  $R_{19}$ is H, a $C_{1-4}$ alkyl, $X_2$ or benzyl;
  $R_{20}$ is H, a $C_{1-10}$ alkyl or —$C(O)R_{21}$,
    wherein $R_{21}$ is H, a $C_{1-4}$ alkyl or alkoxy, t-butoxy or benzyloxy;
  $X_2$ and $X_3$ are independently selected halogens;
  $R_3$ is H, $CH_3$, or —$C(=O)(CR_{15}R_{16})_w$-D,
  where w is 0 or an integer from 1 to about 12, and D is H or as described for $R_1$ and $R_2$.
  J is O NH or S;
  $R_4$, $R_5$, and $R_6$ are independently selected from among H, $CH_3$, $C_2$-$C_{10}$ alkyls, alkenyls or alkynyls which can be substituted or unsubstituted; straight or branched; $C_2$-$C_{10}$ heteroalkyls, heteroalkenyls or heteroalkynyls and halogens;

Z is $NR_7R_8$ or
  wherein $R_7$ is selected from among H, $CH_3$, $C_2$-$C_{10}$ alkyls, alkenyls or alkynyls which can be substituted or unsubstituted; straight or branched; $C_2$-$C_{10}$ heteroalkyls, heteroalkenyls or heteroalkynyls, or $(CR_{23}R_{24})_q$-aryl, or $R_8$;
    wherein $R_{23}$ and $R_{24}$ are independently H or a $C_1$-$C_{10}$ alkyl;
    q is an integer from 1 to about 6;
  $R_8$ is selected from among $(CR_9R_{10})_n$—$NR_{22}$—$R_{11}$, $(CR_9R_{10})_n$—$CH_2$—$NHC(O)R_{26}$ and $(CR_9R_{10})$—$CH_2$-E,
    wherein $R_9$ and $R_{10}$ are independently selected from among H, $CH_3$, $C_2$-$C_{10}$ alkyls, alkenyls or alkyls which can be substituted or unsubstituted; straight or branched;
  $C_2$-$C_{10}$ heteroalkyls, heteroalkenyls or heteroalkynyls and halogens;
  $R_{26}$ is A, $CH_3$, O-t-butyl, O-benzyl;
  E is OH, SH or O—$C(O)R_{27}$,
    wherein $R_{27}$ is a $C_1$-$C_6$ alkyl, benzyl or phenyl;
  $R_{22}$ is H or $CH_3$;
  n is a positive integer from 1 to about 10;
  $R_{11}$, is H or -L-B
    wherein L is a linker; and
    B is a first active moiety, containing reactive group moieties such as maleimidyl or N-hydroxysuccinimidyl, etc., or a polymer;
  $R_{25}$ is H, —$C(O)$—$R_{28}$ or —$C(O)$—O—$R_{29}$,
    wherein $R_{28}$ is a $C_1$-$C_6$ alkyl or benzyl; and $R_{29}$ is $CH_3$, t-butyl or benzyl;
  $X_1$ is O, NH, or S; and
  A is H or a second active moiety, designated as either $A_1$ or $A_2$ herein, it being understood that $X_1$ is an integral part of either $A_1$ or $A_2$.

Pharmaceutically acceptable salts, including Cl⁻, Br⁻, $HSO_{-4}$, etc. of compounds corresponding to Formula (I) are also provided.

In preferred aspects, B is a polymer or natural or synthetic organic molecule, a protein, such as an antibody or fragment thereof a carbohydrate, a nucleic acid, a lipid, or other naturally occurring or synthetic compounds.

In further preferred embodiments, A is $A_1$, and $X_1A_1$ is a substrate or substrate analog such as an amino acid, an amino acid derivative, a peptide, a peptide derivative or a substrate or substrate analog for serine proteases, cysteine proteases, esterases, lipases, or other enzymes containing an active site serine or cysteine. In some preferred aspects, $X_1A_1$ is:

in which $R_{12}$ and $R_{13}$ are H or electron donating or electron withdrawing groups and W is a covalent bond. Alternatively, $A_1$ can also be an amino acid or amino acid derivative, peptide or peptide derivative or other molecule which is a substrate or substrate analog for serine proteases, cysteine proteases, esterases, lipases, or other enzymes containing an active site serine or cysteine.

In other aspects of the invention, H—$X_1A_2$ is an enzyme such as a serine protease, cysteine protease, esterase, lipase, or other enzyme containing an active-site serine, cysteine or tysine whose side-chain —O, —S or —NH corresponds to $X_1$ of Formula (I) which is bonded to the C(O) of the Z-CINN upon displacement of $X_1A_1$. Thus, H—$X_1A_2$ is an enzyme rendered inactive through its bond to Z-CINN and is preferably capable of having its enzyme activity restored by hydrolysis or by exposure to light or other energy source.

In still further aspects of the invention, Z-CINN-$X_1$-$A_1$ compositions are derivatized utilizing the reactive Z site of Formula I. In particular, when $R_8$ is $(CR_9R_{10})$—$NR_{22}$—$R_{11}$, and $R_{11}$ is L-B, the artisan is provided with Z-CINN cores which are linked to, among other things, polymers such as PEG or other activated polymers.

Alternatively, the Z-CINN-$X_1$-A can be joined to a linker group L so that subsequent attachment of B groups, e.g. monoclonal antibodies (mAbs), polymers, etc. can be carried out when desired. The Z-CINN-$X_1$-A can be linked using, for example, succinimidyl-6-[(β-maleimidopropionamido)hexanoate], ethylene glycol bis[succinimidyl succinate], bis activated PEGs containing terminal succinimidyl succinates, N-hydroxy-succinimidyls and/or maleimides. Other bifunctional reagents are also contemplated. The L-Z-CINN-$X_1$-A molecules can then be reacted with another molecule, e.g. proteins, including antibodies, fragments thereof, nucleic acids, lipids, or other naturally occurring or synthetic compounds. Derivatized compositions (B-L-Z-CINN-$X_1$-$A_1$) can then be reacted with an enzyme to form B-L-Z-CINN-X-$A_2$, where the enzyme is inactivated.

As a result of the present invention, several advantages are provided. For example, these Z-CINN-$X_1$-A inactivated compositions can have various beneficial properties, such as increased solubility, increased half-life in circulation, targeting ability, or other features. In addition, L-Z-CINN-$X_1$-A inactivated compositions can be immobilized by crosslinking to support materials via the linker L. The support materials can be any industrially or pharmaceutically suitable materials such as organic polymers, inorganic polymers, natural polymers, biopolymers or zeolites and can be in the form of films, membranes, filters, beads, particles, resins, microparticles, or columns. Alternatively, B-L-Z-CINN-$X_1$-A can be attached to supports by mechanisms such as affinity or by additional coupling reactions with activated support materials.

The acyl-enzyme bonds can be relatively stable or susceptible to hydrolysis at about neutral pH in the dark. They are susceptible to cleavage by a source of energy such as light, including ultraviolet, visible, and infrared light, microwave, ultrasound, radiowave energy or radioactivity. The preferred energy source is light having a wavelength in the range from 340 to 700 nm and preferably 350 to 420 nm. This provides, for example, a means to controllably release and convert inactivated, acylated enzymes to active enzymes.

Compounds of the invention corresponding to, for example, B-L-Z-CINN-$X_1$-$A_2$, can be used in an assay, where the acyl-enzyme is first free or bound to an immobilized support, then energy is applied to release the active enzyme into solution. The inactivated compositions can also be used in purification methods, and as therapeutics, which are activated at the time of or shortly before administration. The inactivated enzymes can be stored for lengthy periods, then reactivated at time of use, to increase shelf lives.

In further aspects of the invention, methods of preparing and using the compositions of the present invention are also provided.

DETAILED DESCRIPTION OF THE INVENTION

I. Definitions

Figure 1:
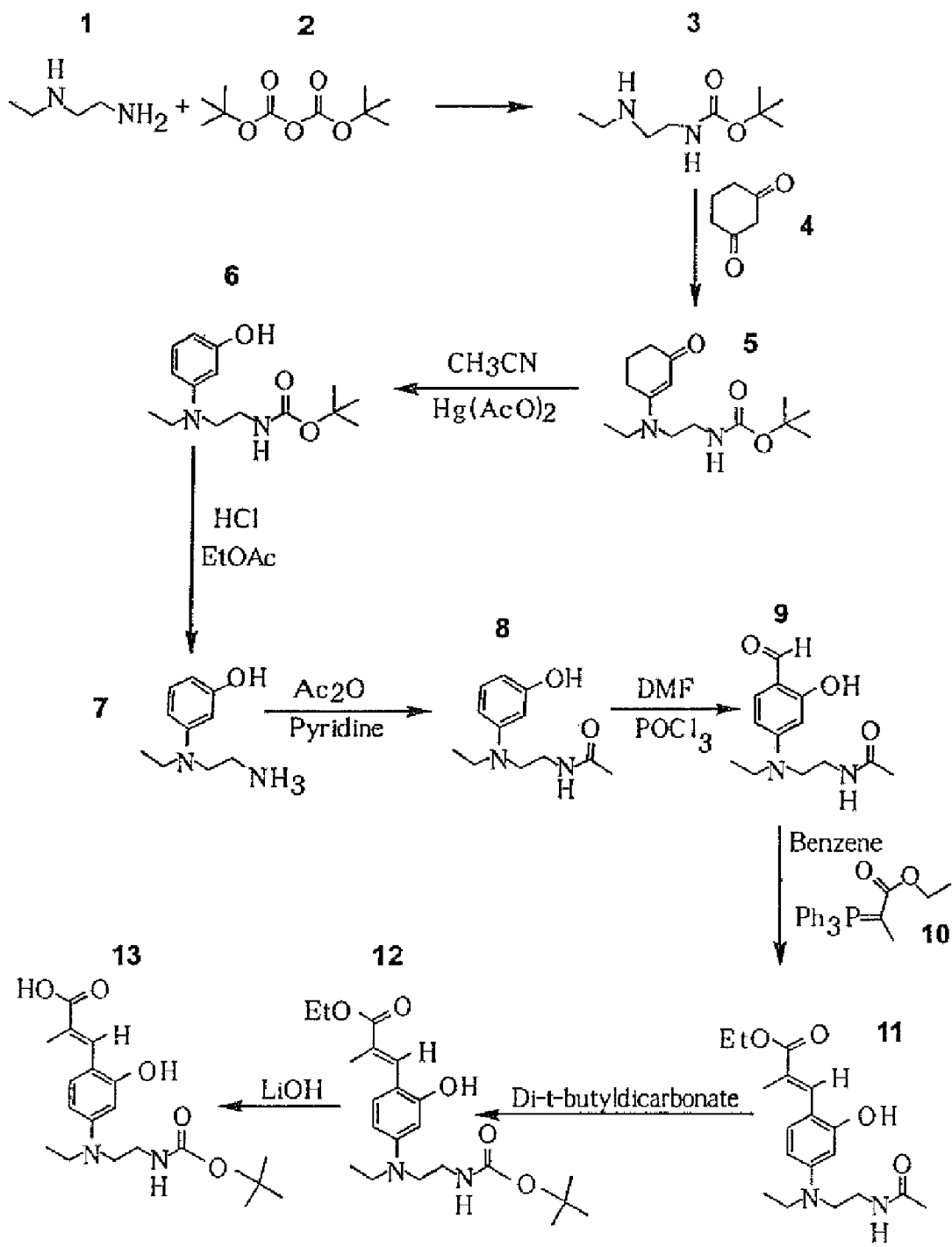
FIG. 1 illustrates the synthesis of (3-[2-hydroxy-4-(ethyl) (2-tert-butylcarbamidoethyl)amino]phenyl-2-methyl-2-propenoic acid, ethyl ester) (10).

The term "inhibitor" as used herein means a compound which can react with a residue at the catalytically active site of an enzyme to inactivate the enzyme by binding to the site and preventing catalytic activity.

The term "inactivated" as used herein means that the catalytically active site of an enzyme is covalently coupled to an inhibitor.

The term "reactivation" as used herein refers to the process in which the covalent acyl bond is cleaved by hydrolysis, or by a source of energy, and enzyme activity is restored.

The term "cinnamic acid" is the common or trivial name for 3-phenyl-2-propenoic acid. Z-CINN-$X_1$-A molecules include derivatives of cinnamic acid.

IUPAC names are given for synthesized compounds.

For purposes of the present invention "reactive group", particularly as used to describe the variable B shall be understood to include those moieties capable of facilitating conjugation of L and one or more biologically active moieties or polymers, including but not limited to the free electron pair (double bond) of a maleimidyl residue.

For purposes of the present invention, the terms "alkyl", "alkenyl" and "alkynyl" shall be understood to include, e.g., straight, branched, substituted, cyclo-derivatives thereof, including alkoxy or substituted cycloalkyls, etc. "Substituted" shall be understood to include halo-, alkoxy-, nitro-, etc.

For purposes of the present invention, "molecule" and "biologically active molecule" shall be understood to embrace not only organic or small molecules but also proteins, peptides and the like.

For purposes of the present invention, "halogen" shall be understood to include chlorine, fluorine, bromine, etc.

II. Z-CINN Derivatives

A. Z-CINN

Various compositions can be formed using Z-CINN as a core molecule. A variety of functional groups can be introduced into Z-CINN to modify its chemical as well as physical properties. These compositions can also have different reactivities toward a nucleophile or light. Some preferred inhibited compositions are discussed in detail as follows.

The Z-CINN core molecule corresponds to Formula (II)

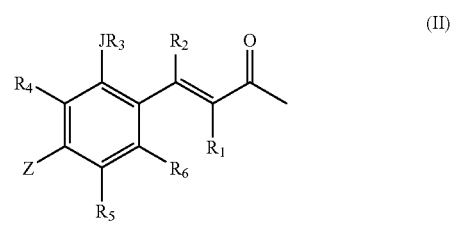

wherein all variables are as set forth in Formula (I) above.

In one preferred embodiment for Formulas (I) and (II), Z is $NR_7R_8$. Further, $R_1$, $R_2$, $R_3$, $R_4$, $R_5$, and $R_6$ are H or lower alkyl groups such as $CH_3$ or $CH_2CH_3$. In another preferred embodiment for Formulas (I) and (II), $R_7$ is $CH_3CH_2$ and $R_8$ is —$(CR_9R_{10})_n$—$NR_{22}$—$R_{11}$, and $R_9$ and $R_{10}$ are H; wherein n is 2; $R_{22}$ is H or $CH_3$; and $X_1$ is O, S or N. In those aspects of the invention where J is O and Z is $NR_7R_8$, some preferred $R_8$ groups include:

1. $(CH_2)_n$—$NH_2$ and salts thereof, e.g. —$NH_3{}^{3\oplus}$:$Cl^-$ or $Br^-$ or $HSO_4{}^-$, etc.
2. $(CH_2)_n$—NH—C(O)—H
3. $(CH_2)_n$—NH—C(O)—$CH_3$
4. $(CH_2)_n$—NH—C(O)—O-t-butyl
5. $(CH_2)_n$—NH—C(O)—O-benzyl
6. $(CH_2)_n$—OH
7. $(CH_2)_n$—SH 8. (CH$_2$)$_n$—O—C(O)—R$_{21}$; wherein R$_{21}$ is CH$_3$, C$_{1-6}$ alkyl or phenyl; wherein each of the above n is an integer of from 2 to about 10, preferably 2-4.

In still a further aspect of the invention, Z is substituted piperazine thereby providing compositions of the Formula (Ia):

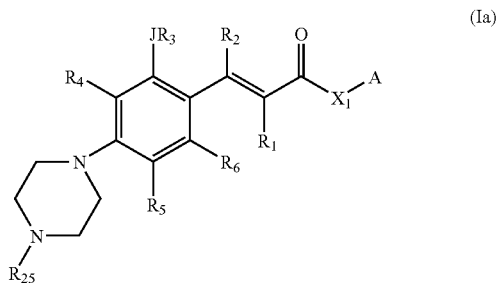

(Ia)

wherein all the variables are as previously defined, with regard to Formula (I).

The cinnamic acid backbone enzyme inhibitors can be synthesized using standard techniques and available reagents by those skilled in the art. For example, as FIG. 1 demonstrates, an amine such as 2-ethylaminoethylamine (1) can react with an anhydride (2) to generate amide (3). 3 condenses with 1,3-cyclohexanedione (4) followed by dehydration to generate 3-amino-2-cyclohexen-1-one (5). Dehydrogenation of 5 in the presence of a catalyst generates a 3-hydroxyphenyl amine (6). Hydrolysis removes a blocking group to obtain 7, followed by N-acylation to obtain 8. Reaction of 8 with POCl$_3$/DMF generates an aldehyde (9). Reaction of 9 with an appropriate Wittig reagent, carbethoxyethylidene triphenylphosphorane (10), generates 11, where the aldehyde group is converted to a 2-propenoic acid ethyl ester. The N-acyl group is exchanged to obtain 12, which is hydrolyzed in LiOH to obtain 13 (tBOC-N-CINN). The compounds of Formula (Ia) can be similarly prepared using piperazine in place of the amine (1).

Figure 2:
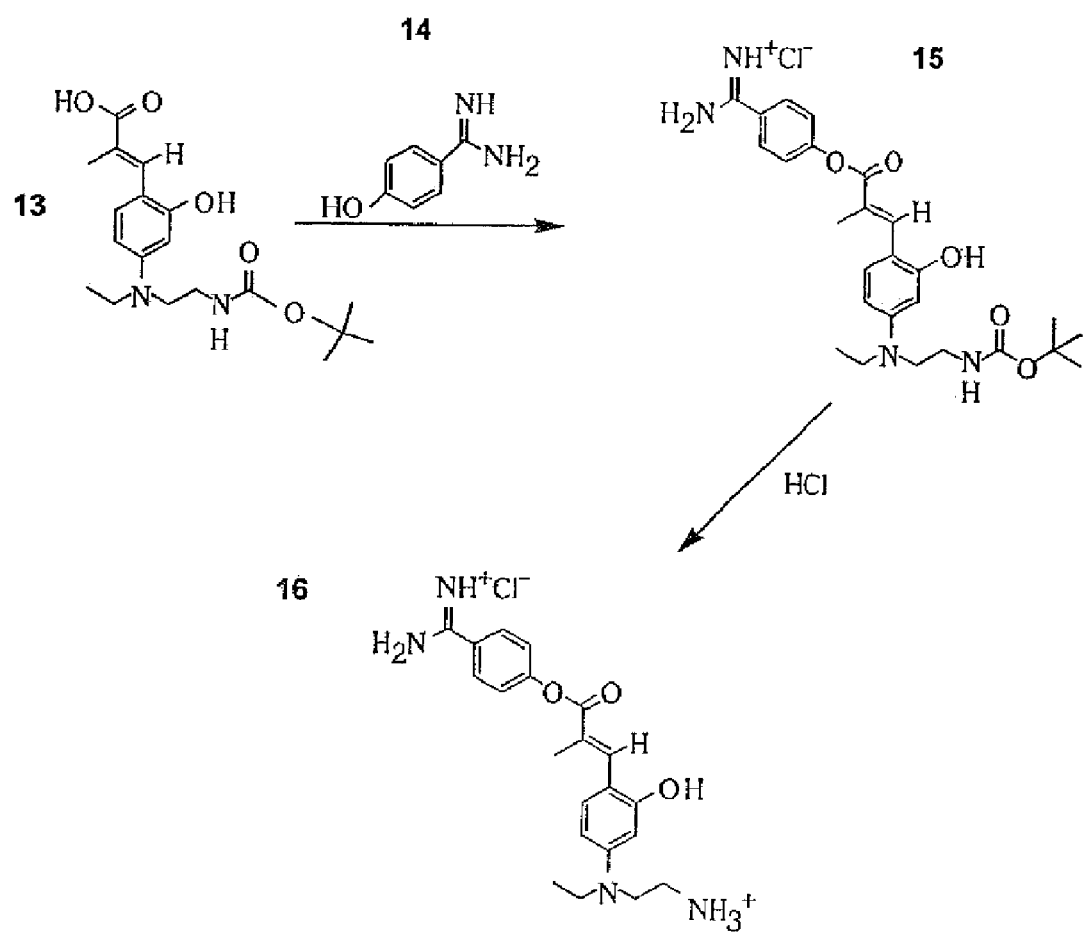
FIG. 2 illustrates the synthesis of (3-[2-hydroxy-4-(ethyl) aminoethyl)-amino]phenyl-2-methyl-2-propenoic acid, 4-aminoiminophenyl ester, HCl salt) (N-CINN-AP) (16).

As FIG. 2 further demonstrates, 13 can be reacted in the presence of an alcohol such as 4-aminoiminophenol (14), dicyclohexylcarbodiimide, and dimethylamninopyridine to form an ester (15). The N-protective group can be hydrolyzed in the presence of HCl to generate a substituted cinnamate ester (enzyme inhibitor) containing a free, protonated amino group (16). As FIG. 3 demonstrates, 16 further reacts with a monomeric SS-PEG (17) to generate PEG-derivatized inhibitor (18).

Figure 4:
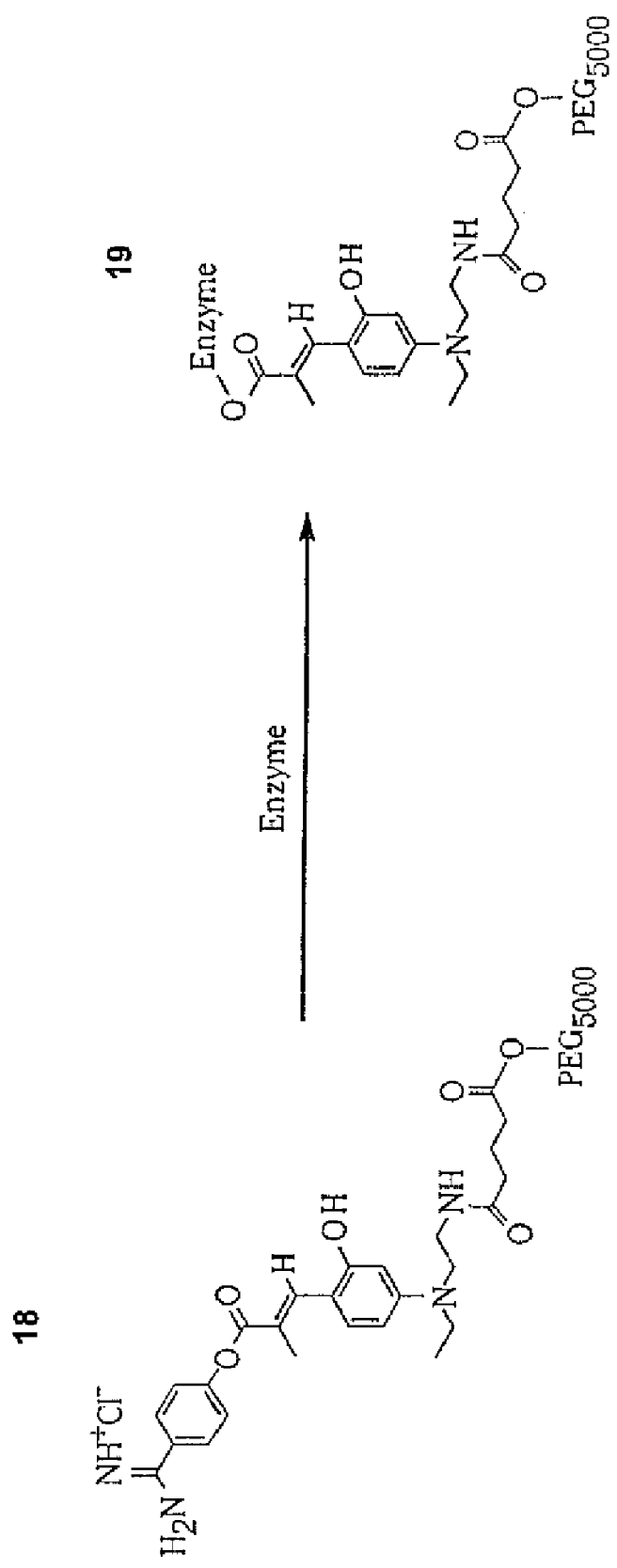
FIG. 4 illustrates the preparation of derivatized inhibited enzyme (19) by reaction of mnPEG$_{5000}$-N-CINN-AP (18) and enzyme.

FIG. 4 further illustrates the reaction of 1 with various enzymes containing active site serines and affinity for 4-aminoiminophenol to obtain inhibited enzyme compositions.

In another embodiment, other alcohols, thiols, or amino compounds, such as amino acids, amino acid derivatives, peptides, or other compounds are used in place of 14 to form additional-X$_1$A$_1$ moieties. For example, an amino acid derivative or peptide derivative is coupled to the N-CINN backbone (13) via the DCI/DMAP chemistry shown in FIG. 2. Carboxyl groups on a peptide or amino acid would be protected with acceptable blocking groups prior to reaction with 13. The amino group would then react with 13, DCI, and DMAP to give an amide bond, and the blocking groups would be removed. Similar procedures would be followed for alcohols or thiols.

Figure 5:
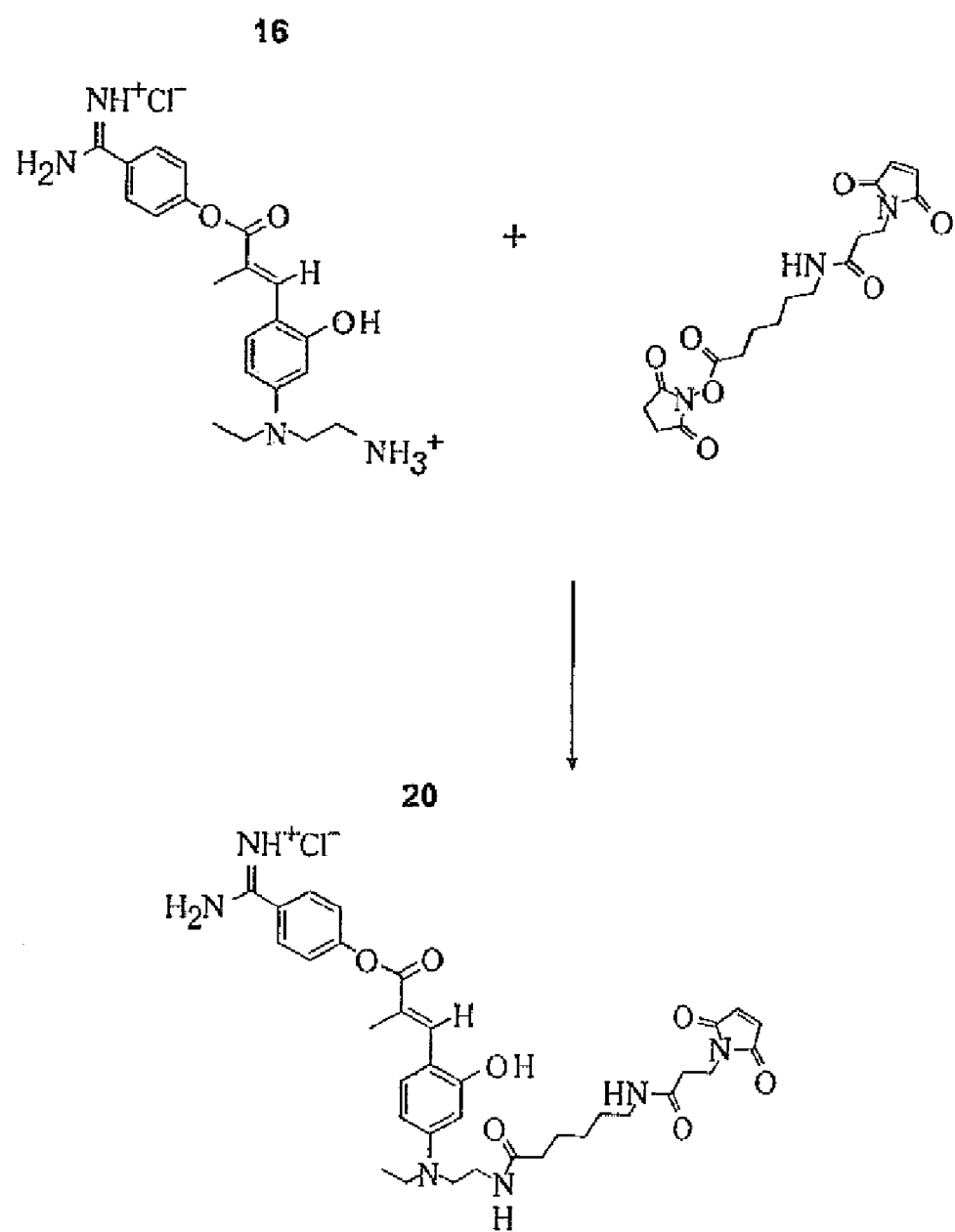
FIG. 5 illustrates the preparation of a maleimido derivative of N-CINN-AP (20), Mal-L-N-CINN-AP, by reaction of (16) with succinimidyl-6-[(β-rnaleimidopropion-amido)hexanoate].

FIG. 5 is the general scheme for preparation of a maleimido derivative of N-CINN-AP (20), by reaction of (16) with a heterobifunctional reagent containing N-hydroxysuccinimide and maleimide. An amino group of 16 reacts with a reagent such as SMPH (succinimidyl-6-[β3-maleimidopropionamido) hexanoate; Pierce); the maleimide group at the other end is available for further reactions. A number of similar reagents are available, for example bifunctional NHS, bifunctional PEGs, or similar compounds. Those skilled in the art will be able to choose appropriate linking reagents to couple the Z-CINN backbone to carrier groups without undue experimentation. For purposes of illustration and not limitation, a non-limiting list of linkers which can be employed include succinimides, maleinides, imidoesters, 2-iminothiolane, hydrazides, maleic anhydride, azides, citraconic anhydride, glutaraldehyde, and the like, which facilitate attachment of any desired B group to the Z-CINN core.

Figure 6:
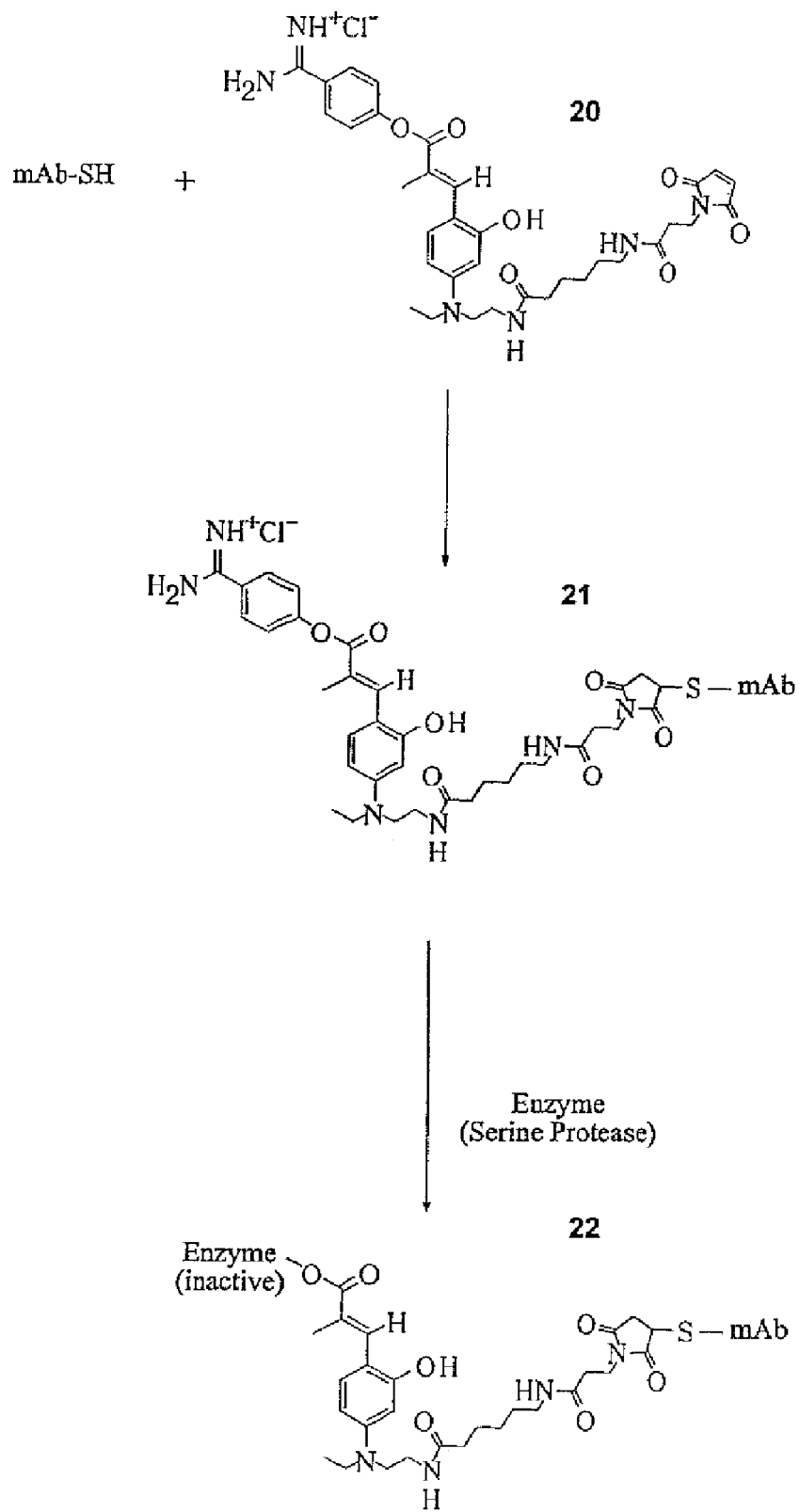
FIG. 6 illustrates the preparation of antibody-L-N-CINN-AP (21) by reaction of SH-modified protein with (20), followed by reaction with enzyme to give antibody-Mal-L-N-CINN-enzyme (22).

FIG. 6 shows that Mal-L-N-CINN-AP (20) can be reacted with a SH-modified antibody to form an antibody-L-N-CINN-AP (21). 21 can be reacted with free enzyme to form antibody-L-N-CINN-enzymne (22), where the enzyme is inhibited. 22 can be treated with light or other energy source to regenerate free enzyme. SH-modified antibody is prepared at~pH 7 using common reagents and the Mal-L-N-CINN-AP is added at~pH 7 in slight excess. Free reagents are separated by ultrafiltration or size exclusion chromatography. In other embodiments, moieties other than SH-modified antibodies are used following the schematic set forth in FIG. 6, with changes in the reactive linking group as required.

B. Inhibition of Enzyme Activity

As defined by Formula I, X$_1$A may include an active moiety. In that formula, the active moiety is referred to as the "second" so as to distinguish it from the first active moiety which is part of B and is discussed in more detail below. Thus, X$_1$A$_2$ can be a biologically active moiety such as an enzyme which has a serine or cysteine residue at the catalytically active site, such as a number of proteases or esterases. The enzyme H—X$_1$A$_2$ can be specifically reacted with Z-CINN-X$_1$-A$_1$, a substrate or substrate analog for the enzymne. A transition state forms, where the enzyme displaces the leaving group in the acyl bond, and an inhibited acyl-enzyme is formed between the Z-CINN and the enzyme, and is designated herein as Z-CINN X$_1$-A$_2$. The inhibited enzyme can be reactivated and recovers its activity when the acyl bond is cleaved by hydrolysis or photolysis.

Exemplary enzymes (H—X$_1$-A$_2$) are serine proteinases (proteases) such as chymotrypsin, trypsin, acrosin, clotting factors such as thrombin, VIIa, IXa, Xa, XIa or XIIa, cathepsin G, fibrinolytic pathway proteins such as plasmin, tissue plasminogen activator, urokinase, streptokinase, and complement proteins such as C3/C5 convertase, complement Factor I, and complement Factor D.

Other exemplary enzymes include cysteine proteinases such as cathepsin B, papain, and bromelain, as well as lipases, and esterases such as acetylcholinesterase.

Preferred serine proteinases include chymotrypsin, trypsin, thrombin, plasmin, acrosin, coagulation factors IXa, Xa, XIa, and XIIa, plasminogen activator, plasma kallikrein, tissue kallikrein, urokinase, plasmin, pancreatic elastase, and leukocyte elastase. Inhibitors are preferably target specific. For example, imidazole derivatives are known as good substrates for α-chymotrypsin. F. Marlkwardt et al., *Phanazie* 29:333 (1974); G. Wagner et al., Pharmazie 28:293 (1973); J. Sturzebecher et al., *Acta Biol, Med. Germ.* 35:1665 (1976); P. Walsmrann, *Folia Haematol., Leipzig* 109:75 (1982); V. Valenty et al., *Biochem. Biophys. Res. Comm.* 88:1375 (1979); and F. Markwardt et al., *Acta Biol. Med. Germ* 28:19 (1972)) describe compounds that lead to stable carboxylate esters of the enzyme active site serine. Other inhibitors that have been studied include compounds that react with the enzyme to generate stable sulfonate or phosphate esters (See R. Laura et at., *Biochemistry* 19:4859 (1980); S. Wong and E. Shaw, *Arch. Biochiem. Biophys.* 161:536 (1974)). Peptide derivatives of phosphonates have also been used (J. Oleksyszyn and JC Powers, *Biochemistry* 15: 485 (1991)).

Alternatively, A can be a moiety designated herein as $A_1$. Preferred $X_1A_1$ groups include

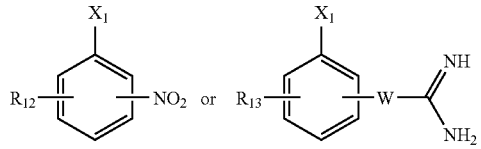

in which $R_{12}$ and $R_{13}$ are electron donating or electron withdrawing groups and W is N or CH, or $X_1A_1$ is an amino acid or amino acid derivative, peptide or peptide derivative, or other substrate or substrate analog of enzymes such as serine proteases, cysteine proteases, or esterases containing an active-site serine or cysteine that can be cleaved by the enzyme, leading to binding of the enzyme to the cinnamoyl moiety as an acyl-enzyme.

Z-CINN-$X_1A_1$ represent inhibitors of the enzymes discussed above. Of the preferred inhibitors, those in which p-nitrophenyl is the leaving group ($X_1A_1$) are preferred for use in making acyl-enzymes with enzymes such as chymotrypsin. Those inhibitors in which either 4-aminoiminophenyl or 4-guanidinophenyl are the leaving groups are preferred for use in making acyl-enzymes with coagulation enzymes, such as thrombin, plasmin, coagulation Factor IXa, Xa, XIa, XIIa, or with tissue plasminogen activator, urokinase, and trypsin. Those in which amino acids or amino acid derivatives, peptides or peptide derivatives, or other substrates or substrate analogs are the leaving groups will react with a variety of enzymes containing serine or cysteine at the active site, including, for example, proteases, lipase, esterases, etc.

C. Derivatives of Z-CINN Backbones

A number of different molecules can be attached to the Z-CINN backbone of the present invention. See Formula (III) below.

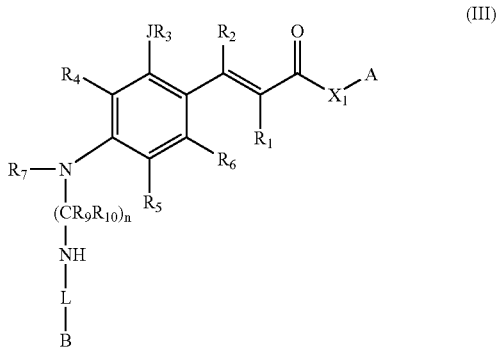

wherein all variables are as previously defined.

In one aspect, moieties can be attached to increase solubility or circulating half-life. For example, an activated polyethylene glycol (PEG) or polypropylene glycol (PPG) can be attached to the Z-CINN core molecule. See U.S. Pat. No. 4,179,337 generally and U.S. Pat. No. 5,612,460 which describes inter alia poly(ethylene glycol)-N-succinimidyl carbonate and derivatives thereof. See also, Poly(ethylene glycol) Chemistry and Biological Applications, Harris, et al., 1997 ACS. The contents of each of the foregoing is incorporated herein by reference. Generally, with reference to FIG. 3, an activated mPEG (for example SS-mPEGG$_{5000}$, Shearwater Polymers, Inc.) is reacted with 16 at ~pH 7.0 for 60 min. Excess SS-mPEG is quenched with glycylglycine and the PEG-N-CINN-AP (18) is reacted with an active serine protease at pH 6.5-7.0 for about 12-16 hours at ambient temperature to give PEG-N-CTNN-acyl-enzyme (19). This complex can be included as part of a pharmaceutically acceptable solution and administered to a patient in need of such therapy. The conjugate is activated with light to release native enzyme when needed. It will be appreciated by those of ordinary skill that the specific type of activated PEG or other polymer employed will be dependent upon the particular needs of the artisan and the final product desired. It is contemplated that most commercially available activated polymers are useable herein without undue experimentation.

More specifically, in order to form the polymer conjugates of the invention, $R_{11}$ may comprise a polymer. For example, polymers such as polyalklyene oxides (PAOs) or similar biologically acceptable polymers are converted into activated forms, as that term is known to those of ordinary skill in the art. Thus, one or both of the terminal polymer hydroxyl endgroups, (i.e. the alpha and omega terminal hydroxyl groups) are converted into the same (homo-) or different (hetero-) reactive functional groups that allow covalent conjugation to the Z-CINN as part of $R_{11}$, and, if desired another active or targeting group. Other substantially non-antigenic polymers are similarly "activated" or functionalized. As an alternative to PAO-based polymers, other substantially non-antigenic or effectively non-antigenic materials such as collagen, glycosaminoglycans, poly-aspartic acid, poly-L-lysine, polylactic acid, copolymers of the foregoing including polylactic-polyglycolic acid copolymers, poly-N-vinylpyrrolidone, collagen cross-linked to hydrophilic polymers or any other suitable non-reactive polymer such as polyethylene alcohols can be used. Specifically preferred polymeric groups are mono or bifunctionally activated polyethylene glycol (PEG) based polymers.

Polymeric groups of any molecular weight range are usable. A preferred polymer molecular weight can range from 2,000 Daltons to 200,000 Daltons. A more preferred molecular weight range is between 5,000 to 50,000 D. The most preferred polymer molecular weight range is between 12,000 and 40,000 D, (number average).

In another embodiment, a first active molecule (B) is attached to L-Z-CINN-$X_1A_1$. For example, a protein such as a monoclonal antibody (mAb) can be linked to a Z-CINN-$X_1A_1$. For example, 16 is reacted with a bifunctional reagent containing both NHS and Mal (Pierce Chemical Co.) at pH~7.0 for 1 hour to give 20 (Mal-L-N-CINN-AP). Excess NHS-Mal reagent is quenched with glycylglycine. 20 is then reacted with SH-modified antibody at pH 7.0 for 2 hours at ambient temperature to give 21 (mAb-L-N-CINN-AP). 21 is freed of excess reagent 20 by ultrafiltration or get filtration chromatography and can then be reacted with a serine protease at pH 6.5 for about 12 to 16 hours to give 22 (mAb-L-N-CINN-acyl-enzyme). 22 (B-L-N-CINN-$X_1A_2$) can be targeted to a site with the mAb, then active serine protease is freed by light activation.

A non-limiting list of reactive group reagents corresponding to L-B of $R_{11}$ include maleimides, N-hydroxysuccinimidyl compounds, imidoesters, 2-iminothiolane, hydrazides, maleic anhydride, and the like, which are available from Pierce Chemical, for example. The foregoing list is merely made for purposes of illustration. Once the reactive group is attached, the L-Z-CINN-$X_1$-$A_1$ can be attached to a desired molecule (B) such as a targeting mAb using standard conjugation techniques. A non-limiting list of suitable molecules include antibodies, fragments thereof, single chain binding antibodies and the like, including moieties that are capable of binding/immobilizing on a particle, for example, Herceptin® (trastuzumab), other monoclonal antibodies, such as those directed to cell surface antigens, murine monoclonal antibodies, proteins, nucleic acids, lectins, lipids, carbohydrates, PAOs, glycosaminoglycans, poly-aspartic acid, poly-L-lysine, polyvinylpyrrolidone, collagen, peptides, hormones, ligands for receptors, and the like. Further specific examples are set forth below: Targeting Agents (including but not limited to the following):

Any Antibody that targets a cell or tumor cell in some capacity;

Monoclonal antibodies (mAbs) with origins from mammals including mice, rats, humans, monkeys, chimeric constructions, etc.;

Single chain antibodies;

These antibodies can be expressed in bacteria, plants, yeast, animals, mammal milk (mouse, goat, sheep, pig, cow, etc), and animal cell cultures including murine, rat, human, hamster, etc.;

Growth factors both natural and recombinant and peptide fractions of growth factors that bind to receptors on the cell surface (EGF, VEGF, FGF, ILGF-I, ILGF-II, TGF)

Interferons both natural or recombinant and peptide fractions of interferons that bind to receptors on the cell surface (IFN-$\alpha$, $\beta$, and $\gamma$) and interferon agonists;

Cytokines, either natural or recombinant, and peptide fractions of cytokines that bind to receptor cell surfaces (IL-1, IL-2, IL-3, IL-4, IL-5, IL-6, IL-7, IL-8, IL-9, IL10, IL-12, IL15, TNF, etc);

Any peptide, natural, recombinant, or synthetic that binds to a cell surface receptor;

Any hormone either natural or synthetic that binds to a cell surface receptor (estrogen, pro-estrogen);

Any metabolite either natural or synthetic that binds to a cell surface receptor (amino acids, sugars, vitamins, nucleotide, nucleoside);

Any lectin either natural or recombinant that binds to the tumor cell surface;

Sugar peptides either phosphorylated or non-phosphorylated (MDP, MTP, DDP, DTP) or sugar-peptide-lipid targeting agent (monophosphoryl Lipid A, diphosphoryl-Lipid A, DPG-DDP, DPG-DTP, etc.);

Polyethylene glycol polymers and derivatives (2,000->200,000 Daltons);

Poly-aspartic or glutamic acids or poly-lysine amino acid polymers or mixtures of these or other amino acids;

Inhibitors peptides or chemical; covalent binding or non-covalent binding) of cell surface enzymes (matrix metalloproteinases inhibitors, tyrosine kinase inhibitors, serine protease inhibitors, casein kinase inhibitors, plasminogen activator inhibitors); and glycoseaminoglycans and dextrans.

As will be apparent to those skilled in the art, those targeting agents not specifically mentioned, but falling within the above categories, are also within the scope of the present invention.

Thus, in one aspect of the invention, preferred $R_{11}$ substituents are proteins such as antibodies to biological materials, which can be used to assist in the localizing of potential enzyme activity prior to release by light or other energy source.

D. Carriers and Supports to Immobilize The Z-CINN Derivatives.

Compounds of Formula (I) including Z-CINN core molecule conjugates of inhibited enzymes can be immobilized on a support made of any of a variety of organic or inorganic materials, including synthetic polymers, natural polymers and biosynthetic polymers. These can be in the form of columns, films, membranes, beads, particles, microparticles, and filters.

Immobilization is generally achieved by formation of a covalent, ionic, or affinty bond between a side chain of the core inhibitor molecule (for example 16, N-CINN-AP) and the support material. For example, a support material containing an aldehyde group or reactive acid group could be used. In one example, agarose beads containing free aldehyde groups (Aldehyde-Agarose; Sigma) are added to 16 at pH~7.0 to form Bead-N-CINN-AP. Excess reagents are washed away and the immobilized inhibitor can then be reacted with a serine protease at pH 6.5 for 12-16 hours at ambient temperature to obtain an immobilized acyl-enzyme, which can be reactivated to give serine protease with light. In another example, agarose beads containing N-hydroxysuccinimidyl groups (Sigma) are added to 16 and processed as above. In another example, utilizing affinity binding, Protein A-Agarose (Sigma or Oncogene) is added to 22 at pH 7, mixed by gentle rocking for 90 min, and separated by centrifugation. The beads are washed several times to remove unbound material and then can be used to bind enzyme as above, and release enzyme activity after exposure to light. These types of binding are within the knowledge of one skilled in the art and can be readily achieved using standard techniques available in the art.

III. Cleavage of Acyl Bond

The covalent acyl bond between the cinnamate core molecule and the therapeutic moiety designated in Formula (I) as "$X_1A_2$" can be cleaved by hydrolysis, naturally occurring in solution or, at a controllable rate, following energy input. A variety of energy forms, including light (ultraviolet, visible, or infrared), ultrasound, microwave radiation, radio energy and radioactive decay can be used. Light is most preferred. Light is readily and selectively controllable by variation of the wavelength, duration or energy of the radiation. The preferred energy source is light having a wavelength in the range from 300 to 420 nm, most preferably between 350 nm and 400 nm.

The acyl bond between the enzyme and the enzyme inhibitor can be susceptible to hydrolysis at neutral pH in the dark. The rate of hydrolysis can be modulated by variation of pH. Its half-life can vary from seconds up to several days, The substituted amino group on the cinnamate ring confers stability to the Z-CINN-acyl-enzyme bond that lasts preferably >24 hr at pH 7.0. This is in contrast to the acyl-enzyme bond reported by King (U.S. Pat. No. 5,770,699) whose hydrolysis rate is designed to be 20-90 minutes. This stability makes the cinnamate based inhibitors useful for therapeutic applications where the inhibited enzyme needs to be kept inhibited in an aqueous system until activation with light. The Z-CINN-acyl-enzyme can therefore also serve as a prodrug carrier if desired which releases the enzyme in vivo without light activation.

Reactivation of the Z-CINN-$X_1$-$A_2$ enzyme is accelerated by light energy. Energy input induces a conformational change in the Z-CINN portion leading to hydrolysis of the acyl-enzyme bond and release of active enzyme. The preferred energy sources have a wavelength in the range from 300 to 420 nm for reactivation times ranging from seconds to minutes. The extent of reactivation depends on such factors as the nature of the inactivated enzyme, the environment, and the type and intensity of the energy source. For example, inactivated thrombin can be readily reactivated by application of white light in a period of about twenty seconds.

The energy source can be introduced via means such as an external visible light source like a focused lamp or laser. A fiber optic catheter that emits light from its tip can deliver light to the target. In other embodiments, the energy source can be introduced in the form of microwave irradiation, radio wave irradiation, ultrasound, radiation of radioactive materials, ultraviolet irradiation, or infrared irradiation.

IV. Methods of Use/Treatment

The compounds disclosed herein have many applications. One general application of pharmaceutical importance uses the bifunctional aspect of the cinnamate backbone to target an enzyme to some specific structure in the body. These structures could be on tumor cells or extracellular, such as a blood clot. Another use is to inhibit an enzyme, which is not needed or desired initially in an application, and reactivate it later in the procedure. The inactivated enzyme can be reactivated by applying light, ultrasound, or other energy source to cleave the acyl bond between the inhibited enzyme and the inhibitor. Another application is to increase the stability or circulatory lifetime of the inhibited enzyme in solution. The amount of the compound administered to a mammal in need of such treatment will of course depend upon the needs of the patient and the enzyme or therapeutic agent administered. It is contemplated that the amount administered will be based on known amounts for the unconjugated enzyme and will be sufficient to successfully treat the mammal.

The compounds of the present invention are thus administered as part of pharmaceutically acceptable formulations e.g. as part of parenteral, i.e. intravenous or oral dosage forms as such are known to those of ordinary skill in the art.

The compounds can be used for purification, particularly those that are immobilized and bind selectively with a target molecule under a given set of conditions, by allowing solutions of the targeted enzyme to equilibrate with inhibitor, then washing away solution before releasing free enzyme following energy input. For example, a compound containing 4-aminoiminophenol at the "A" position could be immobilized and used to isolate thrombin from solution.

The compounds can be used in diagnostic assays. The diagnostic assay may be manual or automated, useful either in laboratories or in the form of a kit.

V. Methods of Synthesis

In another aspect of the invention there are provided methods of preparing the conjugates described herein. Some preferred methods include reacting a compound of Formula (IV):

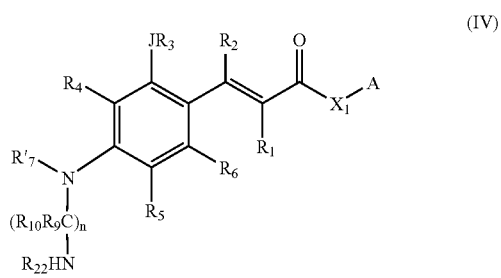

wherein all variables are as defined with respect to Formula (I) and $R'_7$ is selected from among H, $CH_3$ and $C_2$-$C_{10}$ alkyls;

with a compound of the Formula (V)

$$L_1-B_1 \quad (V)$$

wherein $L_1$ is a moiety containing a functional group capable of reacting with the $NH_2$ of Formula IV);

and $B_1$ is polymer, a biologically active material such as an mAb or fragment, etc. polymeric support or the like;

under conditions sufficient to form a conjugate corresponding to Formula (VI)

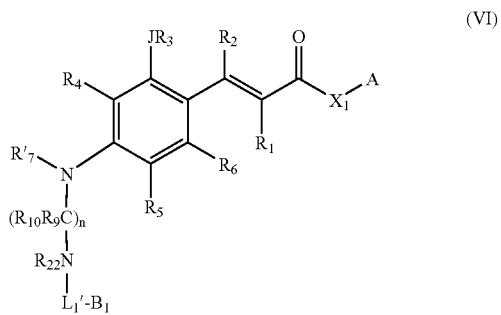

wherein $L_1'$ represents the residue of $L_1$ after the reaction of (IV) with (V). For purposes of the present invention, "conditions sufficient" shall be understood to include not only those conditions set forth in the Examples below but also those conditions, e.g. temperatures, suitable reagents, solvents, etc. associated with achieving the desired final product.

Some particularly preferred compounds of the present invention are set forth in the following examples and figures. See, for example, compounds 16, 18, 20 and 21.

The compounds and methods of use thereof disclosed herein can be further understood by the following non-limiting examples.

VI. EXAMPLES

Many modifications and variations of this invention can be made without departing from its spirit and scope, as will be apparent to those skilled in the art. The specific embodiments described below are offered by way of example only, and the invention is to be limited only by the terms of the appended claims, along with the full scope of equivalents to which such claims are entitled.

Example 1

Synthesis of 3-[2-hydroxy-4-(ethyl)(2-butyloxycarbamidoethyl)-amino]phenyl-2-methyl-2-propenoic acid (13)

Step 1. Synthesis of (2-ethylaminoethylcarbamic acid, 1,1-dimethylethyl ester) (3)

Refer to FIG. 1. A 25g (0.28 mol) quantity of N-ethylethylenediamine (1) was placed in a dried 500 ml rb flask. THF, 250 ml, previously dried by distillation from CaH, was added via cannula. The flask was kept under argon and cooled in an ice bath for 20 minutes. A dried addition funnel was charged with 50 ml THF to which was added 29.3 ml (0.13 mol) of di-tert-butyl dicarbonate (2). This mixture was added slowly dropwise to the stirred amine. After addition was complete, the reaction was removed from the ice bath and allowed to stir and reach ambient temperature overnight. The volatiles were removed by rotary evaporation. Saturated NaCl (50 ml) was added, and the result extracted with 4×100 ml ethyl acetate. The combined organic fractions were dried over $Na_2SO_4$ overnight. The drying agent was removed by filtration and the volatiles removed by rotary evaporation to yield 2-ethylaminoethylcarbamic acid, 1,1-dimethylethyl ester (3; 27.55 g, 0.15 mol). The material was used without further purification.

Step 2. Synthesis of (2-(ethyl)(3-cyclohex-2-ene-1-one)aminoethylcarbamic acid, 1,1-dimethylethyl ester) (5)

A 200 ml quantity of benzene was added to 27.5 g (0.15 mol) 2-ethylaminoethylcarbamic acid, 1,1-dimethylethyl ester (3) in a 500 ml rb flask. The flask was equipped with a Dean-Stark trap and condenser. The mixture was brought to reflux under argon and 18 g (1.1 eq.) of 1,3-cyclohexanedione (4) was added all at once. The benzene/water layer was removed from the trap, about 75 ml overall. The trap was rinsed with acetone, dried briefly and quickly replaced and filled with freshly activated 4A molecular sieves and the reaction allowed to proceed overnight. The reaction was cooled to ambient temperature under argon. The volatiles were removed by rotary evaporation to yield a red-orange oil, which may solidify on standing. The material (2-(ethyl)(3-cyclohex-2-ene-1-one)aminoethylcarbamic acid, 1,1-dimethylethyl ester; 5) was used without further purification.

Step 3. Synthesis of (2-(ethyl)(2-hydroxyphenyl)aminoethylcarbamic acid, 1,1-dimethylethyl ester) (6)

To 0.15 mol crude 2-(ethyl)(3-cyclohex-2-ene-1-one)aminoethylcarbamic acid, 1,1-dimethylethyl ester (5) was added 300 ml $CH_3CN$, freshly distilled from CaH. The mixture was brought to reflux under argon and 1.1 eq. mercuric acetate, $Hg(AcO)_2$, was added in one portion. The suspension was stirred at reflux overnight under argon. Reaction was accompanied by a color change to a claret solution, a violet precipitate and elemental Hg. The reaction was allowed to cool to ambient temperature under argon and was then transferred to centrifuge tubes and centrifuged at 3000 rpm for 10 minutes. The supernatant solutions were removed and combined. Additional $CH_3CN$ was added to the tubes; the solid precipitate was resuspended and centrifuged as above. The supernatants were pooled with those previously obtained. The volatiles were removed by rotary evaporation. The dark purple isolate was transferred to a separatory funnel with a minimal volume of chloroform and the resulting solution was washed with 5% $NaHCO_3$ until the pH of the aqueous layer was about 7. The organic layer was removed and two additional extractions were performed with chloroform, followed by three extractions with ethyl acetate. The organic fractions were combined, dried over $Na_2SO_4$ and freed of volatiles by rotary evaporation. The crude material obtained in this way can be stored under argon at −80° C. for up to several days. A 680 g quantity of silica was mixed with 134 g decolorizing charcoal, slurried with hexane and poured into a 100 mm glass column with about 190 mm of packing. The crude isolate was loaded in a minimum volume of chloroform (3×50 ml). The elution was performed at 7-10 psi with ethyl acetate/hexane: 1.5 L, 20%; 1.5 L, 30%; 1.5 L, 40%; 1 L, 50%. Fractions were pooled and volatiles removed by rotary evaporation to leave a slightly yellowish oil. The material (2-(ethyl)(2-hydroxyphenyl)aminoethylcarbamic acid, 1,1-dimethylethyl ester; 6) exhibits behavior consistent with sensitivity to air and light at this point and must be handled accordingly. It was successfully stored at −20° C. under argon for a period of one month. Yield: 8.78 g (21% for two steps).

Step 4. Synthesis of (3-(ethyl)(2-acetylaminoethyl)aminophenol)(8)

Degassed ethyl acetate (75 ml) was added to 5.5 g (19.6 mmol) 2-(ethyl)(2-hydroxyphenyl)aminoethylcarbamic acid, 1,1-dimethylethyl ester (6). To this was added 50 ml of 3N HCl and the reaction was stirred at ambient temperature overnight. TLC analysis was done using 30% EtOAc/hexanes. The reaction mixture was tranferred to a separatory funnel and extracted with 2×40 ml 1N HCl. The pooled aqueous layers were placed on the rotary evaporator and the volatiles removed. Water was added (about 50 ml) and removed by rotary evaporation, 2 cycles. The resulting oil was frozen in dry ice and placed under vacuum, then allowed to warm naturally to remove all volatiles. The resulting crispy material (7) was used without further purification, and kept free of air and moisture. Dry pyridine (75 ml) was added to the isolate by cannula. The flask was swirled to dissolve the material. Acetic anhydride (1.2 eq.) was added via syringe and the reaction was stirred under argon at ambient temperature. TLC analysis was performed with 10% methanol/chloroform. At the completion of the reaction, the pyridine was removed by rotary evaporation and the residue treated with 100 ml of 10% NaOH by stirring overnight under argon. The reaction was adjusted to pH 9 with 1N HCl and extracted with 4×75 ml ethyl acetate. The combined organic layers were washed with water, then brine (once each), pre-dried with $Na_2SO_4$, then dried overnight with $MgSO_4$. The solution was collected by filtration and the volatiles were removed by rotary evaporation. The material was purified by flash chromatography on silica: loaded with 5% methanol/chloroform; eluted with 150 ml each of 3.3, 6.6, and 9.9% solvent as above to give 3-(ethyl)(2-acetylaminoethyl)aminophenol (8). Yield was 4.2 g (96%).

Step 5. Synthesis of (2-hydroxy4-(ethyl)(2-acetylaminoethyl)aminobenzaldehyde) (9)

A scrupulously dry flask was charged with anhydrous DMF (15 ml) and cooled in ice under argon. Phosphorus oxychloride, $POCl_3$, 1.5 ml (1.15 eq) was added slowly dropwise to the stirred solution. After the addition was complete, the flask was removed from the ice bath and allowed to reach ambient temperature. This was accompanied by a color change to yellow. The flask was heated in a 40° C. bath for one hour. It was removed from the heat, and once at ambient temperature, a DMF solution of 3-(ethyl)(2-acetylaminoethyl)aminophenol (8; 3.2 g, 14 mmol) was added via addition funnel. After the addition was complete, the flask was returned to the 40° C. bath and stirred overnight. The reaction was cooled to 0° C. and 25 ml 10% NaOH was added, the mixture was allowed to warm to ambient temperature and was then placed in a 40° C. bath. Additional NaOH was added to achieve pH >10. Water (50 ml) was added. After 15 minutes the flask was removed from the bath and the pH adjusted to 5-5.5 with 1N HCl. The mixture was transferred to a separatory funnel and extracted with 4×100 ml ethyl acetate. The pooled organic fractions were washed with water (1×75 ml), predried with $Na_2SO_4$, and then dried with $MgSO_4$ overnight. The solution was collected by filtration and the volatiles removed by rotary evaporation to yield the crude product (2.9 g). The material was purified by flash chromatography on silica, 45×150 mm column, eluting with 200 ml each of 2.5%, 5%, and 10% methanol/chloroform purified yield of(2-hydroxy-4-(ethyl)(2-acetylaminoethyl)aminobenzaldehyde) (9) was 1.52 g (45%).

Step 6. Synthesis of (3-[2-hydroxy-4-(ethyl)(2-acetylaminoethyl)amino]phenyl-2-methylpropenoic acid, ethyl ester) (11)

2-hydroxy-4-(ethyl)(2-acetylaminoethyl)aminobenzaldehyde (9;1.58 g, 6.3 mmol) was placed in a flask with degassed benzene (50 ml). Carbethoxy(ethylidene)triphenylphosphorane (10;1.05 eq.) was added and the reaction stirred overnight under argon. The reaction was freed of volatiles by rotary evaporation, then purified by flash chromatography (silica, 95 mm×45 mm), eluting with 250 ml 2.5%; 150 ml 5%; and 150 ml 10%; all methanol/chloroform to give 3-[2-hydroxy-4-(ethyl)(2-acetylaminoethyl)amino]phenyl-2-methylpropenoic acid, ethyl ester (11). The yield was quantitative.

Step 7. Synthesis of (3-[2-hydroxy4-(ethyl)(2-tert-butyloxycarbamidoethyl)-amino]phenyl-2-methylpropenoic acid, ethyl ester) (12)

3-[2-hydroxy-4-(ethyl)(2-acetylaminoethyl)amino]phenyl-2-methylpropenoic acid, ethyl ester (11; 2.0 g, 6 mmol) was dissolved in anhydrous THF (30 ml). Di-t-butyldicarbonate (2; 3 eq) and dimethylaminopyridine (0.1 eq) were added and the reaction was heated to 75° C. TLC analysis (silica, 5% methanol/chloroform) was used to gauge reaction completion; after 3.5 hours the reaction was determined to be finished. The solution was allowed to cool to ambient temperature, the volume of the reaction was doubled with anhydrous methanol, and hydrazine (3 eq.) was added dropwise via syringe. The reaction was allowed to stir under argon overnight. The solution was poured into 100 ml $CH_2Cl_2$ in a separatory funnel, and water (100 ml) was added. The mixture was shaken and allowed to separate; the water layer was adjusted to pH 4.5 by judicious addition of 1N HCl, shaking well after each addition. The aqueous layer was cloudy but colorless. After thorough washing, the layers were separated and the organic layer washed with aqueous $NaHCO_3$ at pH 7.8-8.0. The organic layer was dried by stirring overnight over $MgSO_4$. The solution was collected by filtration and the volatiles were removed by rotary evaporation. The material was purified by flash chromatography on silica, using 400 ml 15% and 300 ml 30% ethyl acetate/hexane to give 3-[2-hydroxy-4-(ethyl)(2-tert-butyloxycarbamidoethyl)amino]phenyl-2-methylpropenoic acid, ethyl ester (12). The yield was 1.7 g (72%).

Step 8. Synthesis of 3-[2-hydroxy-4-(ethyl)(2-tert-butyoxycarbamnidoethyl)-amino]phenyl-2-methylpropenoic acid (13)

3-[2-hydroxy-4-(ethyl)(2-tert-butyloxycarbamidoethyl) amino]phenyl-2-methylpropenoic acid, ethyl ester (12;759 mg, 1.9 mmol) was taken up in ethanol (10 ml). A 5 ml quantity of 10% w/v LiOH was added and the reaction was heated to 40° C. under argon. The reaction was complete after 6 hours, determined by TLC. The mixture was allowed to cool to ambient temperature, the pH adjusted to 5-6 with 1N HCl, and extracted into ether (4×50 ml); the combined organic layers were washed with saturated $NH_4{}^+Cl^-$ and dried over $CaSO_4$ overnight. The solution was collected by filtration and the volatiles were removed by rotary evaporation to give 3-[2-hydroxy-4-(ethyl)(2-tert-butyloxycarbamidoethyl) amino]phenyl-2-methylpropenoic acid (13). The material was used without further purification. Yield was 509 mg (74%).

Example 2

Preparation of 3-[2-hydroxy-4-(ethyl)aminoethyl) amino]phenyl-2-methylpropenoic acid, 4-aminoiminophenyl ester, HCl salt (16; N-CINN-AP)

Step 1. Synthesis of 3-[2-hydroxy-4-(ethyl)(2-tert-butyloxycarbamidoethyl)amino]-phenyl-2-methylpropenoic acid, 4-aminoiminophenyl ester, HCl salt (15; tBOC-N-CINN-AP)

Refer to FIG. 2. 3-[2-hydroxy-4-(ethyl)(2-tert-butyloxycarbamidoethyl)-amino]phenyl-2-methylpropenoic acid (13) (509 mg; 1.4 mmol) was dissolved in anhydrous pyridine. Dicyclohexylcarbodiimide (1.2 eq.), 4-aminoiminomethylphenol hydrochloride (14; 1.1 eq.) and dimethylaminopyridine (0.05 eq.) were added and stirred at ambient temperature under argon for 12-16 hr. The reaction mixture was passed through a medium porosity sintered glass filter, and freed of volatiles by rotary evaporation. The isolate was taken up in 5% methanol/chloroform, filtered, and freed of volatiles as above. The crude material, 15, was purified by flash chromatography on silica, loading with 3 ml 5% and eluting with 100 ml 5%; 75 ml 10%; 75 ml 15%; and 200 ml 20%; all methanol/chloroform. Yield was 448 mg (66%).

Step 2. Synthesis of 3-[2-hydroxy-4-(ethyl)aminoethyl) amino]phenyl-2-methylpropenoic acid, 4-aminoiminophenyl ester, HCl salt (16; N-CINN-AP)

3-[2-hydroxy-4-(ethyl)(2-tert-butyloxycarbamidoethyl) amino]phenyl-2-methylpropenoic acid, 4-aminoiminophenyl ester, HCl salt (15; 12 mg, 25 μmmol) was suspended in 1.2 ml of 3N HCl and mixed by inversion for 3 hours at ambient temperature to release the t-BOC group and generate 3-[2-hydroxy-4-(ethyl) aminoethyl)amino]phenyl-2-methylpropenoic acid, 4-aminoiminophenyl ester, HCl salt (16; N-CINN-AP). After 3 hours, the reaction was neutralized with 3N NaOH to give a final pH of 7.0. This material was used immediately and was not characterized further except that it was now soluble in aqueous solution.

Example 3

Preparation of $mPEG_{5000}$-N-CINN-AP (18)

Figure 3:
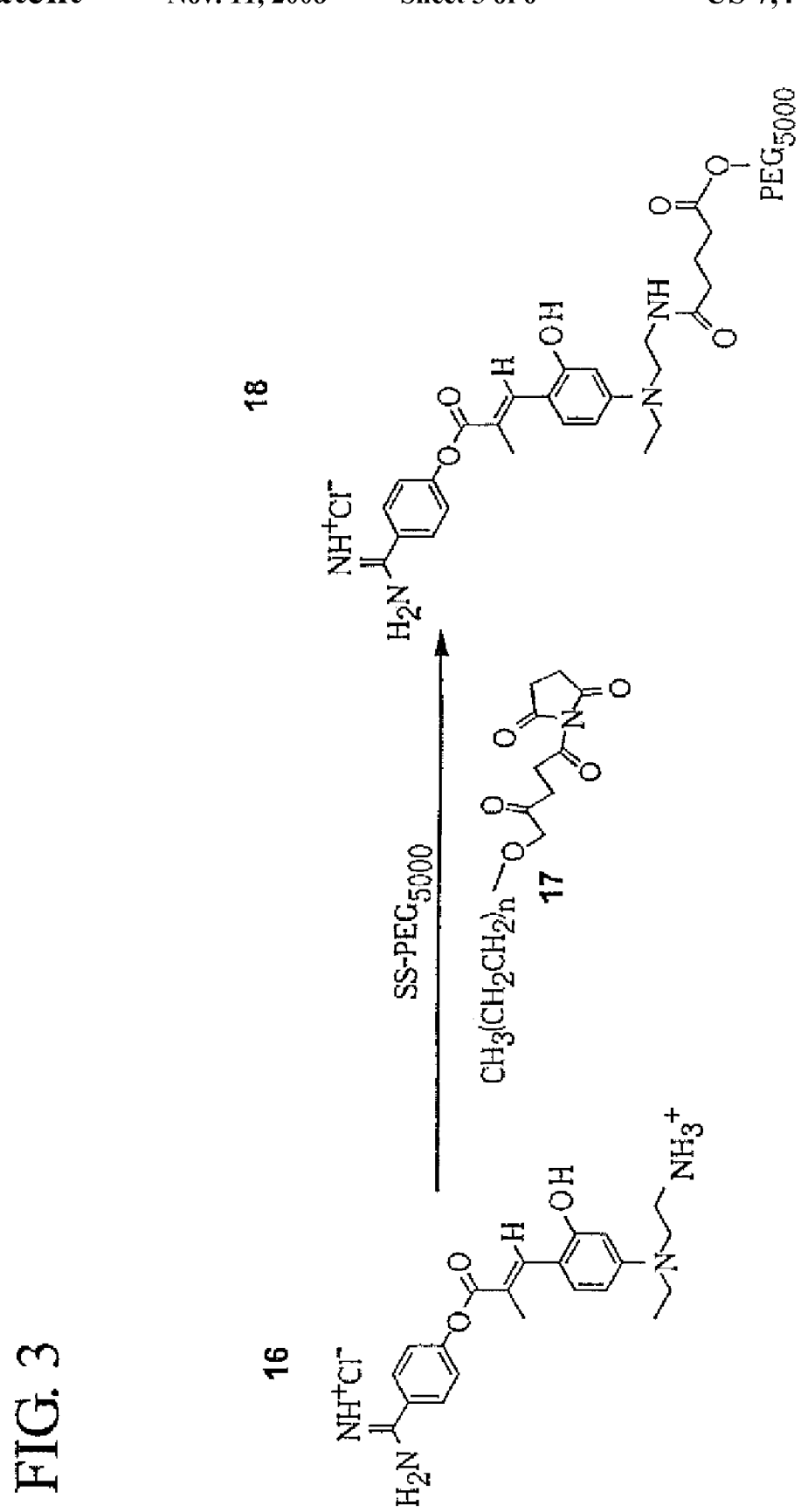
FIG. 3 illustrates the preparation of mPEG$_{5000}$-N-CINN-AP (18).

Refer to FIGS. 3 and 4. $mPEG_{5000}$-SS (2M4R0H01; Shearwater Polymers) was used as follows. 3-[2-hydroxy-4-(ethyl) aminoethyl)amino]phenyl-2-methylpropenoic acid, 4-aminoiminophenyl ester, HCl salt (16; 2.5 mg, 6.5 μmol; pH 7.0-7.4) in 1 ml of 10 mM sodium phosphate buffer, pH 7.2, was added to dry $mPEG_{5000}$-SS (17; 38.3 mg, 7.5 μmol). After 1 hour at ambient temperature, the reaction was stopped by the addition of 75 μM glycylglycine in 100 μl of water. This material ($mPEG_{5000}$-NH-CINN-AP;18) was used within 3 hours for inhibition reactions with serine proteases such as thrombin and tPA.

Example 4

Inhibition of Thrombin with R—NH-CINN-AP Derivatives

R is -tBOC, —$H_2{}^+$, or $mPEG_{5000}$. Human thrombin was modified with R—NH-CINN-AP inhibitors as follows: Thrombin (600 units; ~3.5 nmol) in 50 mM sodium citrate buffer, 3 mM $CaCl_2$, 7% kollidon, pH 7.0, was reacted with 3.5-35 nmol of the R—N-CINN-AP inhibitor for 12-18 hours at ambient temperature in the dark. Thrombin activities were measured under red light ("dark") and after exposure to 10 seconds of blue light from a dental light and were assayed using S-2238 (diaPharma) at 30° C. Percentage inhibition was calculated as 100—dark activity. Dark activity was calculated as [$activity_{dark} \div activity_{control}$]×100. Light reactivation was calculated as $activity_{light} \div activty_{control}$. The following are typical results.

TABLE 1

Inhibition and Reactivation of R-N-CINN-Acyl-Thrombin[a]

| Inhibitor | Inhibitor Excess | Inhibition after 16 Hrs Incubation (%) | Light Reactivation (%) |
| --- | --- | --- | --- |
| None | 0 | 0 | NP |
| CINN-AP | 1× | 53 | NP |
| CINN-AP | 5× | 99 | NP |
| CINN-AP | 10× | 99 | 60 |
| #15 | 1× | 94 | NP |
| #15 | 5× | 98 | NP |
| #15 | 10× | 97 | 72 |
| #16 | 1× | 21 | NP |
| #16 | 5× | 70 | NP |
| #16 | 10× | 96 | 64 |
| #18 | 2× | 51 | NP |
| #18 | 10× | 98 | 69 |

[a]Thrombin activity was assayed as described in Chromogenic Substrates (Chromogenix AB Information Manual) using S-2238 (H-D-Phe-Pip-arg-pNA•2HCl) as the synthetic substrate.
15 = tBOC-N-CINN-AP
16 = $NH_3$-CINN-AP
18 = $mPEG_{5000}$-N-CINN-AP
NP = Assay not performed The R—NH-CINN-AP compounds inhibit thrombin, as does the parent compound CINN-AP. All of the acyl-thrombins can be reactivated with blue light, indicating that the modifications to create R—NH-CINN-AP do not affect the ability of the molecule to isomerize and release free enzyme from the acyl-enzyme. The $NH_3$-CINN-AP, which contains a positive charge, appears to be a less effective inhibitor at lower molar ratios. The $mPEG_{5000}$-NH-CINN-AP, which contains a 5000 dalton linear mPEG molecule, requires higher concentrations to effect thrombin inhibition. These results show that one can alter other portions of the molecule without losing the effects of a light reversible, covalent inhibitor. Light reactivation remains essentially the same, indicating that the R—NH-CINN-acyl-thrombin molecule absorbs blue light energy and can isomerize to give the cis configuration and release active thrombin.

Example 5

Inhibition of Tissue Plasminogen Activator (tPA) with $R_z$—NH-CINN-AP Derivatives $R_2$ is -tBOC, —$H_2^+$, or $mPEG_{5000}$. The procedures of Examnple 4 was repeated except that Human tPA (Activase, Genentech Inc. Lot # E9034A) was modified with $R_z$—NH-CINN-AP inhibitors in place of thrombin. The reactions were carried out as follows: tPA (0.83 nmol) in 10 mM tris-HCl, 130 mM NaCl, pH 7.4 was reacted with 0.8 3-8.3 nmoles of the R—NH CINN-AP inhibitors for 12-18 hours at ambient temperature in the dark. Activities were calculated as for Example 4, using S-2288 (diaPharna). The results are provided below.

TABLE 2

Inhibition and reactivation of $R_z$-N-CINN-tPA[a]

| Inhibitor | Inhibitor Excess | Inhibition after 16 hrs incubation (%) | Light Reactivation (%) |
| --- | --- | --- | --- |
| None | 0 | 0 | NP |
| CINN-AP | 5× | 95 | NP |
| CINN-AP | 10× | 95 | 82 |
| #15 | 5× | 95 | NP |
| #15 | 10× | 95 | 87 |
| #16 | 5× | 78 | NP |
| #16 | 10× | 88 | 78 |

[a]tPA activity was assayed as described in Chromogenic Substrates (Chromogenix AB Information Manual) using S-2288 (H-D-Ile-Pro-Arg-pNA•2HCl) as the synthetic substrate
15 = tBOC-N-CINN-AP
16 = $NH_3$-CINN-AP
NP = Assay not performed The $R_z$—NH-CINN-AP compounds inhibit tPA, as does the parent compound CINN-AP. All of the acyl-tPAs can be reactivated with blue light, indicating that the 30 modifications to create R—NH-CINN-AP do not affect the ability of the molecule to isomerize and release free enzyme from the acyl-enzyme. The $NH_3$-CINN-AP, which contains a positive charge, appears to be a less effective inhibitor at lower molar ratios. These results show that other portions of the molecule can be altered without losing the effects of a light reversible, covalent inhibitor. Light reactivation remains essentially the same, indicating that the R—NH-CINN-acyl-tPA molecule absorbs blue light energy and can isomerize to give the cis configuration and release active tPA.

Example 6

Preparation of N-CINN-AP with Maleimide Linker (20)

N-CINN-AP (16; 10 μmoles, 1 ml) was reacted with 11.4 μmoles of SMPH (succinimidyl-[β-maleimidopropionamido] hexanoate; Pierce #22363) in 0.5 ml DMSO and 0.5 ml 200 mM sodium phosphate, pH 7.4 for 2 hours at ambient temperature. After 2 hours, the reaction was placed on ice, and unreacted NHS was quenched with 0.05 ml of 100 mM glycylglycine. The final product (20) was used within 2 hours, and was not further characterized.

Example 7

Preparation of Antibody-Linker-N-CINN-AP (21)

A monoclonal antibody, Herceptin® (trastuzumab, Genentech) was prepared at 5 mg/ml in phosphate-NaCl buffer, pH 7. SATA (N-succinimidyl S-acetylthioacetate; Pierce) was dissolved in DMSO and a 20-fold molar excess was added to the protein and reacted for 1 hour. Hydroxylamine HCl (Pierce; 0.5 M, neutralized to pH 7.0) was added for 60-90 minutes, and antibody was separated from low molecular weight material by chromatography on D-SALT Polyacrylamide desalting columns (Pierce) equilibrated in phosphate-NaCl buffer. Incorporation of thiols into antibody (antibody-SH) was determined using Ellman's reagent (Pierce). 20, at a 2-fold molar excess to incorporated-SH groups, was added to Antibody-SH for 2 hours at pH 7.4 and ambient temperature to give 21. Antibody-containing fractions (21) were separated from excess 20 on a D-SALT column as above.

Example 8

Preparation of Antibody-Linker-N-CINN-Enzyme (22)

21 was mixed with thrombin (400 U/ml; Enzyme Research Labs) at pH 7.0 for 12-16 hours at ambient temperature to form 22, and 22 was separated from free enzyme by binding to Protein A-Agarose beads (Oncogene) which had been washed 3 times with phosphate-NaCl buffer. After gentle mixing for 90 min, the beads were washed by centrifulgation 3 times and supernatants containing unbound enzyme were removed. Beads were suspended in assay buffer at pH 8.3 containing 0.5 mM S-2238 (Chromogenix), and assayed for 6 min at 30° C. Ten seconds of blue light from a ProLite dental light was then directed to the wells, and assays were continued for another 6 min. The rate of S-2238 cleavage increased 7-8 fold on exposure to light, indicating release of free thrombin into solution.

Example 9

Preparation of Antibody-PEG-N-CINN-AP (23)

N-CIN-AP (16, 2.4 µmoles, 1.0 ml) in 50 mM sodium phosphate buffer, pH 7.0, was reacted with 4.8 µmoles of $PEG_{3400}$-(SPA)$_2$ (PEG succinimidyl propionate; Shearwater Polymers, Inc) in 1 ml WFI at ambient temperature for 1 hour. The SPA-PEG-N-CINN-AP was immediately reacted with goat anti-rabbit IgG (Calbiochem, 401311) as follows: 10.6 nmoles of SPA-PEG-N-CINN-AP was reacted with 2.6 moles antibody for 2 hours at pH 7.0 at ambient temperature. The reaction mixture was placed on ice and excess SPA was quenched with 0.05 ml of 100 mM glycylglycine. The product was used within two hours, and not further characterized.

Example 10

Preparation and Assay of Antibody-PEG-N-CINN-Acyl-Thrombin (24)

Antibody-PEG-N-CINN-AP (23) was mixed with thrombin (400 U/ml; Enzyme Research Labs) at pH 7.0 for 16 hours at ambient temperature. The antibody-acyl-enzyme complex was then tested for its ability to bind to its antigen and release active enzyme. Rabbit IgG (Calbiochem) was bound to polystyrene plates following standard procedures. The plates were then blocked with PBS/Tween 20/BSA (Sigmna) for 2 hours, and washed extensively with PBS/Tween 20 to remove excess protein. Goat anti-rabbit antibody-PEG-N-CINN-Acyl-Thrombin (24) was then allowed to bind to the rabbit IgG on the plate for 2 hours at ambient temperature. The plates were then washed 5 times with PBS/Tween 20 to remove any unbound antibody-thrombin or free thrombin. The plates were assayed for thrombin activity using the S-2238 chromogenic assay described in Example 8. The rate of S-2238 cleavage increased 5 fold after 10 seconds of light activation indicating release of free thrombin into solution.

Examples 11-13

Murine nAbs as Targeting Agents

The following examples provide details regarding the preparation of specific murine mAb-AZ-CINN conjugates and their utility as targeting agents for therapeutic indications.

Example 11

Lung Cancer

A. Preparation of Antibody-Linker-CINN-Enzyme and Its Use

N-CINN-AP (16,2.4 µmoles, 1.0 ml) in 50 mM sodium phosphate buffer pH 7.0 is reacted with 4.8 µmoles of NHS-$PEG_{3400}$-MAL (Shearwater Polymers, Inc. NHS-Mal-3400) dissolved in DMSO. The reaction mixture is rocked for two hours at ambient temperature. The reaction is stopped by the addition of 100 µl of 100 mM glycylglycine. The Mal-$PEG_{3400}$-N-CINN-AP is used within two hours and not further characterized.

B. Preparation of Antibody-PEG-N-CINN-Acyl-Thrombin

A murine monoclonal antibody, BR110 (Hellstrom et.al. U.S. Pat. No. 5,840,854) is diluted to 5 mg/ml in phosphate-NaCl buffer, pH 7. SATA (N-succinimidyl S-acetylthio-acetate; Pierce) is dissolved in DMSO and a 20-fold molar excess is added to the protein and reacted for 1 hour. Hydroxylamine HCl (Sigma; 0.5 M, neutralized to pH 7.0) is added for 60-90 minutes, and antibody is separated from low molecular weight material by chromatography on D-SALT Polyacrylamide desalting columns (Pierce) equilibrated in phosphate-NaCl buffer. Incorporation of thiols into the murine antibody (antibody-SH) is determined using Elman's reagent (Pierce). Mal-$PEG_{3400}$-N-CINN-AP at a 2-fold molar excess to incorporated-SH groups, is added to BR110-mAb-SH for 2 hours at pH 7.4 and ambient temperature to give BR110-mAb-S-Mal-$PEG_{3400}$-N-CINN-AP. Antibody-containing fractions (BR110-mAb-S-Mal-$PEG_{3400}$-N-CINN-AP) are separated from excess Mal-$PEG_{3400}$-N-CINN-AP on a D-SALT column (Pierce) buffered with 50 mM sodium phosphate pH 6.5 and 150 mM NaCl. The antibody-drug (BR110-mAb-S-Mal-$PEG_{3400}$-N-CINN-AP) is concentrated to 5 mg/ml protein using Centricon YM-30 membranes and sterile filtered (0.22 µm filter; Gelman Sciences, Supor Acrodisc 25). BR110-mAB-S-Mal-PEG-N-CINN-AP is mixed with thrombin (400 U/ml; Enzyme Research Labs) at pH 7.0 for 16 hours at ambient temperature. The antibody-acyl-enzyme complex is then separated from free thrombin and concentrated to 5 mg/ml protein using Centricon YM-100 membranes and sterile filtered (0.22 µm filter; Gelman Sciences, Supor Acrodisc 25).

C. Treatment of Human Lung Carcinoma with BR110-mAb-S-Mal-PEG3400-N-CINN-Acyl-Thrombin MAb BR110 is a murine mAb to a 66-kDa glycoprotein that is found on the cell surface of human lung, colon and breast tumor cells. Human lung carcinoma cell line H2987 is grown in cell culture as described (U.S. Pat. No. 5,840,854). $1 \times 10^7$ cells/ mouse are implanted s.c. into a nude mice. When the tumors reach 150-200 mm³ in size, BR110-mAb-S-Mal-$PEG_{3400}$-N-CINN-Acyl-Thrombin is used to treat the tumor as follows; 1.0 mg of BR 110-mAb-S-Mal-$PEG_{3400}$-N-CINN-Acyl-Thrombin (1 mg mAb protein with 27 nmoles thrombin covalently attached) is injected i.v. via tail vein into mice with the tumor. After 6 hours, mice that are given the BR110-mAb-S- Mal-$PEG_{3400}$-N-CINN-Acyl-Thrombin are anesthetized with a Ketamine/Rompun mixture. A 16G needle is used to create a hole in the skin and a 1 mm fiber optic probe is inserted up to the tumor. The tumor is exposed to white light for 5 minutes with a power of about 0.5 mW/cm². Other treatment groups do not receive light treatment. All mice are kept under "red lights" to prevent light activation of the drug, for 72 hours post injection, then returned to nominal light/dark cycle. Tumors in groups that receive light treatment shrink immediately (>50% in 7 days) and are necrotic. Tumors that are treated with BR110-mAb-S-Mal-$PEG_{3400}$-N-CINN-Acyl-Thrombin but do not receive light stimulation shrank at a much slower pace and are smaller than 100 mm³ at 28 days. Groups that receive antibody and free drug (unlinked) show tumor growth, and by 28 days the mice either die or have tumors >800 mm³.

Example 12

Colon Cancer

A. Preparation of Antibody-Linker-CINN-Acyl-Thrombin

Mal-PEG$_{3400}$-N-CINN-AP is prepared as described above in Example 11A.

B. Preparation of Antibody-PEG-N-CINN-Acyl-Thrombin

The procedure of Example 11B is repeated except that MAb A7, a murine mAb to a 45-kDa glycoprotein found on human colon cancer cells, is used in place of the BR110-mAb to produce A7-mAb-S-Mal-PEG$_{3400}$-N-CINN-Acyl-Thrombin.

C. Treatment of Human Colon Carcinoma with A7-mAb-S-Mal-PEG$_{3400}$-N-CINN-Acyl-Thrombin Human colon carcinoma cell line LS-180 is grown in cell culture as described (Kinuya et. al. 2001. J. Nucl. Med. 42:596-600). $1 \times 10^7$ cells/mouse are implanted s.c. into nude mice. When the tumors reach 150-200 mm$^3$ in size, A7-mAb-S-Mal-PEG$_{3400}$-N-CINN-Acyl-Thrombin is used to treat the tumor as follows; 1.0 mg of A7-mAb-S-Mal-PEG$_{3400}$-N-CINN-Acyl-Thrombin (1 mg mAb protein with~27 nmoles of thrombin covalently attached) is injected i.v. via tail vein into mice with the tumor. After 6 hours, mice that are given the A7-mAb-S-Mal-PEG$_{3400}$-N-CINN-Acyl-Thrombin are anesthetized with a Ketamine/Rompun mixture. A 16 G needle is used to create a hole in the skin and a 1 mm fiber optic probe is inserted up to the tumor. The tumor is exposed to white light for 5 minutes with a power of about 0.5 mW/cm$^2$. Other treatment groups do not receive light treatment. All mice are kept under "red lights" to prevent light activation of the drug, for 72 hours post injection, then returned to normal light/dark cycle. Tumors in groups that receive light treatment shrink immediately (>50% in 7 days) and are necrotic. Tumors that are treated with A7-mAb-S-Mal-PEG$_{3400}$-N-CN-Acyl-Thrombin but do not receive light stimulation shrink at a much slower pace and are smaller than 100 mm$^3$ at 28 days. Groups that receive antibody and free drug (unlinked) show tumor growth, and by 28 days the mice either die or have tumors>800 mm$^3$.

Example 13

Breast Cancer

A. Preparation of Antibody-Linker-CINN-Acyl-Thrombin

Mal-PEG$_{3400}$-N-CINN-AP is prepared as described above.

B. Preparation of Antibody-PEG-N-CINN-Acyl-Thrombin

The procedure of Example 11B is repeated except that MAb NR-LU-10, a murine mAb to a pancarcinoma glycoprotein found on human breast cancer cells, is used in place of the BR110-mAb to produce NR-LU-10 S-Mal-PEG$_{3400}$-N-CINN-Acyl-Thrombin.

C. Treatment of Human Breast Carcinoma with NR-LU-10 mAb-S-Mal-PEG$_{3400}$-N-CINN-Acl-Thrombin Human breast cancer xenografts are prepared as described (Burak et.al. 1998. Nucl. Med. Biol. 25:633-637) Xenografts are implanted s.c. into nude mice. When the tumor reaches 150-200 mm$^3$ in size, NR-LU-10 mAb-S-Mal-PEG$_{3400}$-N-CINN-Acyl-Thrombin is used to treat the tumor as follows; 1.0 mg of NR-LU-10 mAb-S-Mal-PEG$_{3400}$-N-CINN-Acyl-Thrombin (1 mg mAb protein with~27 nmoles of thrombin covalently attached) is injected i.v. via tail vein into mice with the tumor. After 6 hours, mice that are given the NR-LU-10 mAb-S- Mal-PEG$_{3400}$-N-CINN-Acyl-Thrombin are anesthetized with a Ketatine/Rompun mixture. A 16 G needle is used to create a hole in the skin and a 1 mm fiber optic probe is inserted up to the tumor. The tumor is exposed to white light for 5 minutes with a power of about 0.5 mW/cm$^2$. Other treatment groups do not receive light treatment. All mice are kept under "red lights" to prevent light activation of the drug, for 72 hours post injection, then returned to normal light/dark cycle. Tumors in groups that receive light treatment shrink immediately (>50% in 7 days) and are necrotic. Tumors that are treated with NR-LU-10 mAb-S-Mal-PEG$_{3400}$-N-CINN-Acyl-Thrombin but do not receive light stimulation shrink at a much slower pace and are smaller than 100 mm$^3$ at 28 days. Groups that receive antibody and free drug (unlinked) show tumor growth, and by 28 days the mice either die or have tumors>800 mm$^3$.

The various publications, patents, patent applications and published applications mentioned in this application are hereby incorporated by reference herein.

What is claimed is:

1. A compound of the formula:

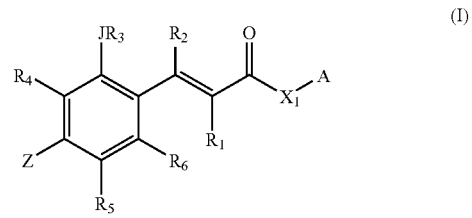

(I)

wherein:

$R_1$ and $R_2$ are individually selected from the group consisting of H, $CH_3$, $C_2$-$C_{10}$ alkyls, $C_2$-$C_{10}$ alkenyls or $C_2$-$C_{10}$ alkynyls, straight or branched;

$C_2$-$C_{10}$ heteroalkyls, $C_2$-$C_{10}$ heteroalkenyls or $C_2$-$C_{10}$ heteroalkynyls and —$(CR_{15}R_{16})_p$-D;

wherein:

$R_{15}$ and $R_{16}$ are individually selected from the group consisting of H, $CH_3$, $C_2$-$C_{10}$ alkyls, $C_2$-$C_{10}$ alkenyls or $C_2$-$C_{10}$ alkynyls, straight or branched; and $C_2$-$C_{10}$ heteroalkyls, $C_2$-$C_{10}$ heteroalkenyls or $C_2$-$C_{10}$ heteroalkynyls;

p is a positive integer from 1 to about 12;

D is selected from the group consisting of —SH, —OH, $X_2$, —CN, —$OR_{19}$, $NHR_{20}$,

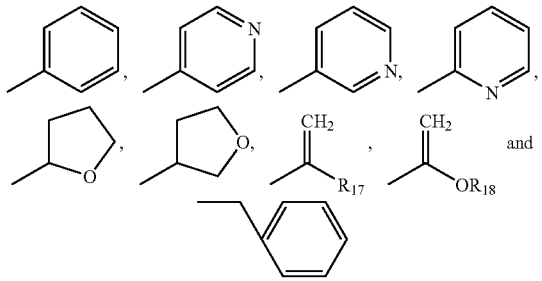

wherein:

$R_{17}$ is H, $CH_3$ or $X_3$;

$R_{18}$ is H, a $C_{1-4}$ alkyl or benzyl;

$R_{19}$ is H, a $C_{1-4}$ alkyl, $X_2$ or benzyl;

$R_{20}$ is H, a $C_{1-10}$ alkyl or —$C(O)R_{21}$, wherein $R_{21}$ is H, a $C_{1-4}$ alkyl or alkoxy, t-butoxy or benzyloxy;

$X_2$ and $X_3$ are independently selected halogens;

$R_3$ is H, $CH_3$, or $-C(=O)(CR_{15}R_{16})_w$-D,
where w is 0 or an integer from 1 to about 12, and D is H or as described for $R_1$ and $R_2$;

J is O, NH or S;

$R_4$, $R_5$, and $R_6$ are independently selected from the group consisting of H, $CH_3$, $C_2$-$C_{10}$ alkyls, $C_2$-$C_{10}$ alkenyls or $C_2$-$C_{10}$ alkynyls, straight or branched; $C_2$-$C_{10}$ heteroalkyls, heteroalkenyls or heteroalkynyls and halogens;

Z is $NR_7R_8$ or

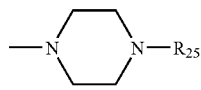

wherein $R_7$ is selected from the group consisting of H, $CH_3$, $C_2$-$C_{10}$ alkyls, alkenyls or alkynyls straight or branched; $C_2$-$C_{10}$ heteroalkyls, heteroalkenyls or heteroalkynyls, or $-(CR_{23}R_{24})_q$-aryl, or $R_8$,
wherein
$R_{23}$ and $R_{24}$ are independently selected from the group consisting of H and $C_1$-$C_{10}$ alkyls;
q is an integer from 1 to about 6;

$R_8$ is selected from the group consisting of $(CR_9R_{10})_n$-$NR_{22}$-$R_{11}$, $(CR_9R_{10})_n$-$CH_2$-$NHC(O)R_{26}$ and $(CR_9R_{10})_n$-$CH_2$-E;
wherein
$R_9$ and $R_{10}$ are independently selected from the group consisting of H, $CH_3$, $C_2$-$C_{10}$ alkyls, $C_2$-$C_{10}$ alkenyls or $C_2$-$C_{10}$ alkynyls, straight or branched;
$C_2$-$C_{10}$ heteroalkyls, $C_2$-$C_{10}$ heteroalkenyls or $C_2$-$C_{10}$ heteroalkynyls and halogens;
$R_{26}$ is H, $CH_3$, O-t-butyl, O-benzyl;
E is OH, SH or O—$C(O)R_{27}$,
wherein $R_{27}$ is a $C_1$-$C_6$ alkyl, benzyl or phenyl;
$R_{22}$ is H or $CH_3$;
n is a positive integer from 1 to about 10;
$R_{11}$ is H or-L-B,
wherein
L is a positive linker covalently linking $NR_{22}$ to B; and
B is selected from the group consisting of polymers, biologically active materials and polymeric supports;
$R_{25}$ is H, —C(O)—$R_{28}$ or —C(O)—O—$R_{29}$,
wherein $R_{28}$ is a $C_1$-$C_6$ alkyl or benzyl; and $R_{29}$ is $CH_3$, t-butyl or benzyl;

$X_1$ is O, NH, or S; and

A is $A_2$
wherein $X_1A_2$ is an enzyme, or a pharmaceutical salt thereof.

2. The compound of claim 1, wherein Z is $NR_7R_8$.

3. The compound of claim 2, wherein $R_8$ is —$CH_2$—$CH_2$—$NH_2$.

4. The compound of claim 2, wherein $R_8$ is $(CR_9R_{10})_n$—$NR_{22}$—$R_{11}$.

5. The compound of claim 1, wherein L-B is a maleimidyl or an N-hydroxysuccinimidyl compound.

6. The compound of claim 4, wherein $R_{11}$ is a polyalkylene oxide residue.

7. The compound of claim 6, wherein said polyalkylene oxide residue is a polyethylene glycol.

8. The compound of claim 7, wherein said polyethylene glycol has a number average molecular weight of from about 2,000 to about 200,000 daltons.

9. The compound of claim 4, wherein $R_{11}$ is a member of the group consisting of collagen, glycosaminoglycan, poly(-aspartic acid), poly(-L-lysine), poly(-lactic acid), poly-N-vinylpyrolidone and copolymers of poly(-lactic acid) and poly(-glycolic acid).

10. The compound of claim 1, wherein $R_1$, $R_2$, $R_3$, $R_4$, $R_5$, and $R_6$ are independently selected from the group consisting of H, $CH_3$ and $CH_3CH_2$.

11. The compound of claim 4, wherein $R_7$ is $CH_3CH_2$; $R_8$ is —$(CR_9R_{10})_n$—$NR_{22}$—$R_{11}$; and $R_9$ and $R_{10}$ are H; n is 2; and $X_1$ is O, S or NH.

12. The compound of claim 4, wherein $R_7$ is $CH_3CH_2$; $R_8$ is —$(CR_9R_{10})_n$—$NR_{22}$—$R_{11}$ and $R_9$ and $R_{10}$ are H.

13. The compound of claim 1, wherein $A_2$ is an enzyme selected from the group consisting of serine proteases, cysteine proteases, esterases, lipases and enzymes containing an active-site serine or cysteine.

14. The compound of claim 1, wherein J is O, $R_2$ is H, $R_7$ is $CH_3CH_2$; $R_8$ is -$(CR_9R_{10})_n$-$NR_{22}$-$R_{11}$, $R_9$ and $R_{10}$ are H, and n is 2.

15. The compound of claim 13, wherein $X_1A_2$ is an enzyme having an active-site serine or cysteine.

16. The compound of claim 1, wherein $X_1A_2$ is a blood coagulation factor.

17. The compound of claim 1, wherein the enzyme is selected from the group consisting of plasmins, urokinases, and tissue plasminogen activators.

18. A compound of claim 1 selected from the group consisting of;

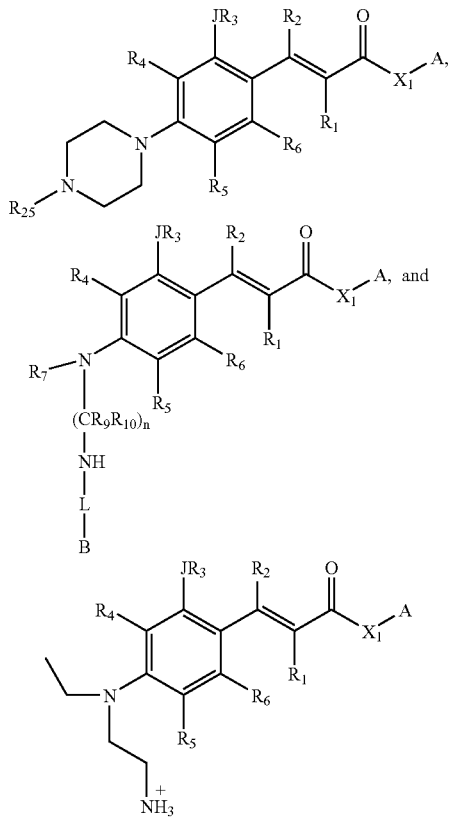

19. A method of treatment, comprising:

administering to a mammal in need of such treatment an effective amount of a compound of formula (I)

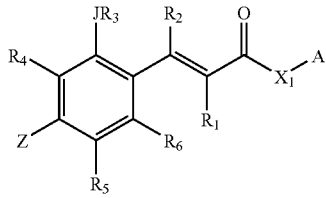

wherein;

$R_1$ and $R_2$ are individually selected from the group consisting of H, $CH_3$, $C_2$-$C_{10}$ alkyls, $C_2$-$C_{10}$ alkenyls or $C_2$-$C_{10}$ alkynyls. straight or branched;

$C_2$-$C_{10}$ heteroalkyls. $C_2$-$C_{10}$ heteroalkenyls or $C_2$-$C_{10}$ heteroalkynyls and -$(CR_{15}R_{16})_p$-D;

wherein:

$R_{15}$ and $R_{16}$ are individually selected from the group consisting of H, $CH_3$, $C_2$-$C_{10}$ alkyls, $C_2$-$C_{10}$ alkenyls or $C_2$-$C_{10}$ alkynyls straight or branched; and $C_2$-$C_{10}$ heteroalkyls, $C_2$-$C_{10}$ heteroalkenyls or $C_{2\text{-}C10}$ heteroalkynyls;

p is a positive integer from 1 to about 12;

D is selected from the group consisting of —SH, —OH, $X_2$, —CN, —$OR_{19}$, $NHR_{20}$,

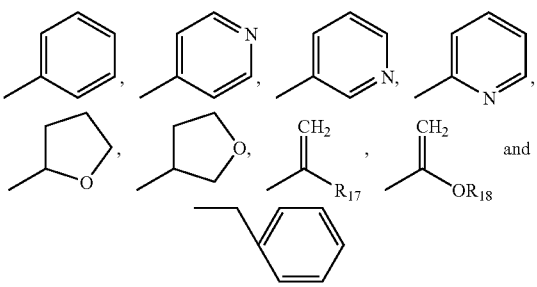

wherein:

$R_{17}$ is H, $CH_3$ or $X_3$;

$R_{18}$ is H, a $C_{1\text{-}4}$ alkyl or benzyl;

$R_{19}$ is H, a $C_{1\text{-}4}$ alkyl, $X_2$ or benzyl;

$R_{20}$ is H, a $C_{1\text{-}10}$ alkyl or —$C(O)R_{21}$, wherein $R_{21}$ is H. a $C_{1\text{-}4}$ alkyl or alkoxy, t-butoxy or benzyloxy;

$X_2$ and $X_3$ are independently selected halogens;

$R_3$ is H, $CH_3$, or —$C(=O)(CR_{15}R_{16})_w$ -D, where w is 0 or an inteiler from 1 to about 12, and D is H or as described for $R_1$ and $R_2$;

J is O, NH or S;

$R_4$, $R_5$, and $R_6$ are independently selected from the group consisting of H, $CH_3$, $C_2$-$C_{10}$ alkyls. $C_2$-$C_{10}$ alkenyls or $C_2$-$C_{10}$ alkynyls, straight or branched; $C_2$-$C_{10}$ heteroalkyls, heteroalkenyls or heteroalkynyls and halogens;

Z is $NR_7R_8$ or

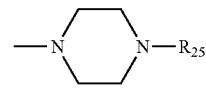

wherein $R_7$ is selected from the group consisting of H, $CH_3$, $C_2$-$C_{10}$ alkyls, alkenyls or alkynyls straight or branched; $C_2$-$C_{10}$ heteroalkyls, heteroalkenyls, or heteroalkynvis, or -$(CR_{23}R_{24})_q$-aryl, or $R_8$, wherein $R_{23}$ and $R_{24}$ are independently selected from the group consisting of H and $C_{1\text{-}C10}$ alkyls;

q is an integer from 1 to about 6;

$R_8$ is selected from the group consisting of $(CR_9R_{10})_D$-$NR_{22}$-$R_{11}$, $(CR_9R_{10})_n$-$CH_2$-$NHC(O)R_{26}$ and $(CR_9R_{10})_n$-$CH_2$-E;

wherein $R_9$ and $R_{10}$ are independently selected from the group consisting of H, $CH_3$, $_2$-$C_{10}$alkyls, $C_2$-$C_{10}$ alkenyls or $C_2$-$C_{10}$ alkynyls, straight or branched;

$C_2$-$C_{10}$ heteroalkyls, $C_2$-$C_{10}$ heteroalkynyls and halogens;

$R_{26}$ is H, $CH_3$, O-t-butyl, O-benzyl;

E is OH, SH or O—$C(O)R_{27}$, wherein $R_{27}$ is a $C_1$-$C_6$ alkyl, benzyl or phenyl;

$R_{22}$ is H or $CH_3$;

n is a positive integer from 1 to about 10;

$R_{11}$ is H or -L-B, wherein

L is a linker covalently linking $NR_{22}$ to B; and

B is selected from the group consisting of polymers. biologically active materials and polymeric supports;

$R_{25}$ is H, —$C(O)$-$R_{28}$ or —$C(O)$-$R_{29}$, wherein $R_{28}$ is a $C_1$-$C_6$ alkyl or benzyl; and $R_{29}$ is $CH_3$, t-butyl or benzyl;

$X_1$ is O,NH, or S; and

A is $A_2$ wherein $X_1A_2$ is an enzyme, or a pharmaceutical salt thereof.

20. The method of claim 19, further comprising exposing the compound of formula (I) to an energy source after administration to said mammal.

21. The method of claim 20, wherein the energy source is white light having a wavelength in the range from 340 to 700 nm.

22. The method of claim 20, wherein the energy source is white light having a wavelength in the range from 350-420 nm.

23. The method of claim 20, wherein the energy source is selected from the group consisting of microwave, ultrasound, radio energy, gamma radiation, radioactivity, ultraviolet light and infrared light.

24. A method of preparing a conjugate, comprising; reacting a compound of Formula (IV)

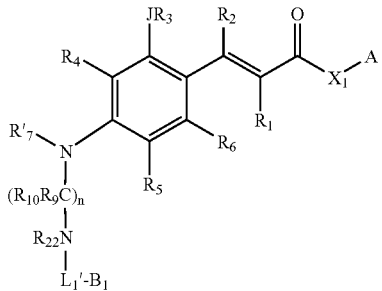

wherein:
$R_1$ and $R_2$ are individually selected from the group consisting of H, $CH_3$, $C_2$-$C_{10}$ alkyls, $C_2$-$C_{10}$ alkenyls or $C_2$-$C_{10}$ alkynyls, straight or branched;
$C_2$-$C_{10}$ heteroalkyls, $C_2$-$C_{10}$ heteroalkenyls or $C_2$-$C_{10}$ heteroalkynyls and —$(CR_{15}R_{16})_p$-D
wherein:
$R_{15}$ and $R_{16}$ are individually selected from the group consisting of H, $CH_3$, $C_2$-$C_{10}$ alkyls, $C_2$-$C_{10}$ alkenyls and $C_2$-$C_{10}$ alkynyls, straight or branched; and
$C_2$-$C_{10}$ heteroalkyls, $C_2$-$C_{10}$ heteroalkenyls or $C_2$-$C_{10}$ heteroalkynyls;
p is a positive integer from 1 to about 12;
D is selected from among —SH, —OH, $X_2$, —CN, —$OR_{19}$, $NHR_{20}$,

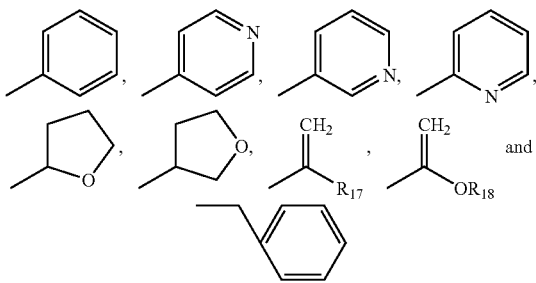

wherein:
$R_{17}$ is H, a $CH_3$ or $X_3$;
$R_{18}$ is H, a $C_{1-4}$ alkyl or benzyl;
$R_{19}$ is H, a $C_{1-4}$ alkyl, $X_2$ or benzyl;
$R_{20}$ is H, a $C_{1-10}$ alkyl or —$C(O)R_{21}$
wherein
$R_{21}$ is H, a $C_{1-4}$ alkyl or alkoxy, t-butoxy or benzyloxy;
$X_2$ and $X_3$ are independently selected halogens;
$R_3$ is H, $CH_3$, or —$C(=O)(CR_{15}R_{16})_w$-D,
where w is 0 or an integer from 1 to about 12, and D is H or as described for $R_1$ and $R_2$,
J is O, NH or S;
$R_4$, $R_5$ and $R_6$ independently selected from the group consisting of H, $CH_3$, $C_2$-$C_{10}$ alkyls, $C_2$-$C_{10}$ alkenyls or $C_2$-$C_{10}$ alkynyls, straight or branched;
$C_2$-$C_{10}$ heteroalkyls, heteroalkenyls or heteroalkynyls and halogens;
$R_7$ is selected from among H, $CH_3$ and $C_2$-$C_{10}$ alkyls;
$R_9$ and $R_{10}$ are independently selected from the group of H, $CH_3$, $C_2$-$C_{10}$ alkyls, $C_2$-$C_{10}$ alkynyls, straight or branched; $C_2$-$C_{10}$ heteroalkyls, $C_2$-$C_{10}$ heteroakynyls, and halogen;
n is a positive integer from 1 to 10;
$X_1$ is O, NH, or S;
$R_{22}$ is H or $CH_3$; and
A is $A_2$
wherein $X_1A_2$ is an enzyme
with a compound of the Formula (V):

$$L_1-B_1 \quad (V)$$

wherein
$L_1$ is a moiety containing a functional group capable of reacting with the $NHR_{22}$ of Formula (IV); and
$B_1$ is selected from the group consisting of polymers, biologically active materials and polymeric supports.

25. The method of claim 24, wherein $L_1$-$B_1$ includes a member selected from the group consisting of heterobifunctional reagents having N-hydroxysuccinimide and maleimide, bifunctional maleimide and bifunctional polyethylene glycol.

26. The method of claim 25, wherein the heterobifunctional reagent is Succinimidyl-6-[(β-maleimidopropionamido) hexanoate].

27. The compound of claim 1, wherein L-B is selected from the group consisting of heterobifunctional reagents having N-hydroxysuccinimide and maleimide, bifunctional maleimide and bifunctional polyethylene glycol.

28. The compound of claim 7, wherein said polyethylene glycol is bifunctional polyethylene glycol.

29. The compound of claim 16, wherein $X_1A_2$ is selected from the group consisting of thrombin (Factor IIa), Factor VIIa, Factor IXa, Factor Xa, Factor XIa and Factor XIIa.

30. The compound of claim 1, wherein L is a linker selected from the group consisting of succinimides, maleimides, imidoesters, 2-iminothiolanes, hydrazides, maleic anhydrides, azides, citraconic anhydrides and glutaraldehydes.

31. The compound of claim 1, wherein B is selected from the group consisting of antibodies, fragments thereof, single chain binding antibodies, monoclonal antibodies, growth factors, interferons, cytokines, cell-surface binding metabolites, lectin, sugar-peptide, sugar-petide-lipid targeting agents, proteins, nucleic acids, lectins, lipids, carbohydrates, inhibitors of cell surface enzymes, PAOs, glycosaminoglycans, dextran, poly-glutamic acid, poly-aspartic acid, poly-L-lysine and mixtures thereof, polyvinylpyrrolidine, collagen, peptides, hormones, ligands for receptors, and carriers and supports in form of columns, films, membranes, beads, particles, microparticles, and filters.

* * * * *